(12) United States Patent
Öhman et al.

(10) Patent No.: US 11,958,049 B2
(45) Date of Patent: Apr. 16, 2024

(54) SAMPLE LOADING CARTRIDGE

(71) Applicant: ASTREGO DIAGNOSTICS AB, Uppsala (SE)

(72) Inventors: Johan Öhman, Uppsala (SE); Martin Lovmar, Mölndal (SE); Lovisa Söderberg, Stockholm (SE); Mikael Olsson, Uppsala (SE)

(73) Assignee: ASTREGO DIAGNOSTICS AB, Uppsala (SE)

( * ) Notice: Subject to any disclaimer, the term of this patent is extended or adjusted under 35 U.S.C. 154(b) by 351 days.

(21) Appl. No.: 17/276,167

(22) PCT Filed: Sep. 20, 2019

(86) PCT No.: PCT/SE2019/050894
§ 371 (c)(1),
(2) Date: Mar. 15, 2021

(87) PCT Pub. No.: WO2020/060475
PCT Pub. Date: Mar. 26, 2020

(65) Prior Publication Data
US 2022/0032302 A1   Feb. 3, 2022

(30) Foreign Application Priority Data
Sep. 20, 2018   (SE) .................... 1851117-0

(51) Int. Cl.
*B01L 3/00* (2006.01)
*B81B 1/00* (2006.01)
*G01N 35/10* (2006.01)

(52) U.S. Cl.
CPC ..... *B01L 3/502746* (2013.01); *B01L 3/50273* (2013.01); *B81B 1/006* (2013.01);
(Continued)

(58) Field of Classification Search
CPC ......... B01L 2200/0621; B01L 2300/02; B01L 2300/0645; B01L 2300/0848;
(Continued)

(56) References Cited

U.S. PATENT DOCUMENTS 4,761,381 A   8/1988   Blatt et al.
7,104,422 B2  9/2006   Dileo
(Continued)

FOREIGN PATENT DOCUMENTS

JP   62-69139 A      3/1987
JP   2006-132991 A   5/2006
(Continued)

OTHER PUBLICATIONS

Wang, Ping et al., Robust Growth of *Escherichia coli*, Current Biology, vol. 20, pp. 1099-1103 (Jun. 22, 2010).
(Continued)

*Primary Examiner* — Jennifer Wecker
*Assistant Examiner* — Jonathan Bortoli
(74) *Attorney, Agent, or Firm* — Porter Wright Morris & Arthur LLP

(57) ABSTRACT

A sample loading cartridge (1) for a microfluidic device comprises a cartridge body (10) with a sample reservoir (20) configured to house a volume of a liquid sample (3) and a sample port (30) in connection with the sample reservoir (20). The cartridge (1) also comprises an output channel (40) extending from the sample reservoir (20) and a feedback channel (50) connected to the sample reservoir (20) and to the sample port (30). The cartridge body (10) comprises a detection portion (60) aligned with the feedback channel (50) to enable detection of any sample (3) in the feedback channel (50). The flow resistance of the feedback channel (50) is lower than the flow resistance of the output channel (40) to cause liquid sample (3) received in the sample port (Continued)

(30) to enter the feedback channel (50) with substantially no liquid sample (3) entering the output channel (40).

22 Claims, 21 Drawing Sheets

(52) U.S. Cl.
CPC .. *G01N 35/1011* (2013.01); *B01L 2200/0621* (2013.01); *B01L 2300/02* (2013.01); *B01L 2300/0645* (2013.01); *B01L 2300/0848* (2013.01); *B01L 2300/087* (2013.01); *B01L 2400/0487* (2013.01); *B81B 2201/057* (2013.01); *B81B 2203/0338* (2013.01)

(58) Field of Classification Search
CPC ....... B01L 2300/087; B01L 2400/0406; B01L 2400/0487; B01L 2400/0688; B01L 3/50273; B01L 3/502746; B01L 3/5027; B81B 1/006; B81B 2201/057; B81B 2203/0338; C12M 23/16; C12M 1/28; C12M 33/00; G01N 33/48707; G01N 33/49; G01N 33/493; G01N 35/1011; G01N 2333/5428; G01N 2333/57; G01N 2800/065; G01N 33/487; G01N 33/6866; G01N 33/6869; A61K 38/00; A61P 1/04; A61P 35/00; C07K 14/5428; C07K 16/283; C07K 2317/31; C07K 2319/00; C07K 2319/30; C12Q 1/6827; C12Q 1/6869; C12Q 1/6883; C12Q 1/6886; C12Q 2600/106; C12Q 2600/156; G16B 25/10; G16B 30/00
See application file for complete search history.

(56) References Cited

U.S. PATENT DOCUMENTS

| | | | |
|---|---|---|---|
| 8,277,764 | B2 | 10/2012 | Gilbert et al. |
| 8,470,588 | B2 | 6/2013 | Boehm et al. |
| 8,679,422 | B2 | 3/2014 | Gilbert et al. |
| 9,784,711 | B2 | 10/2017 | Hoffmeyer et al. |
| 9,823,252 | B2 | 11/2017 | Gilbert et al. |
| 9,915,631 | B2 | 3/2018 | Hoffmeyer et al. |
| 10,222,378 | B2 | 3/2019 | Gilbert et al. |
| 10,794,913 | B2 | 10/2020 | Gilbert et al. |
| 2002/0055167 | A1* | 5/2002 | Pourahmadi ........... C12M 47/06 435/306.1 |
| 2004/0164092 | A1 | 8/2004 | Dileo |
| 2008/0271799 | A1 | 11/2008 | Wimberger-Friedl et al. |
| 2009/0130719 | A1 | 5/2009 | Handique |
| 2009/0253181 | A1* | 10/2009 | Vangbo ............. B01L 3/502738 204/453 |
| 2011/0146390 | A1* | 6/2011 | Gilbert ................. G01N 35/085 73/61.59 |
| 2011/0203700 | A1 | 8/2011 | Scholten et al. |
| 2014/0004505 | A1* | 1/2014 | Su ...................... G01N 33/5304 435/7.37 |
| 2014/0079603 | A1* | 3/2014 | Kanai ............... B01L 3/502738 422/521 |
| 2015/0157797 | A1* | 6/2015 | Eggert .................. A61M 5/343 264/261 |
| 2015/0226397 | A1 | 8/2015 | Konishi et al. |
| 2016/0175836 | A1* | 6/2016 | Taylor ................. B01L 3/50273 422/516 |
| 2017/0137861 | A1* | 5/2017 | Elf ........................ C12Q 1/6874 |
| 2018/0250668 | A1* | 9/2018 | Liang ...................... B01L 3/502 |

FOREIGN PATENT DOCUMENTS

| | | |
|---|---|---|
| JP | 2007-524806 A | 8/2007 |
| JP | 2008-522793 A | 7/2008 |
| JP | 2009-233532 A | 10/2009 |
| JP | 2010-505096 A | 2/2010 |
| JP | 2012-508894 A | 4/2012 |
| JP | 5150328 B2 | 2/2013 |
| WO | 2009/157863 A1 | 12/2009 |
| WO | 2016/007063 A1 | 1/2016 |
| WO | 2016/007068 A1 | 1/2016 |

OTHER PUBLICATIONS

Baltekin, Özden et al., Antibiotic susceptibility testing in less than 30 min using direct single-cell imaging, PNAS, vol. 114, No. 34, pp. 9170-9175 (Aug. 22, 2017).
European Search Report from corresponding European Application No. 19861864.7 dated Jun. 3, 2022.
Office Action from corresponding Japanese Application No. 2021-513239 dated Jun. 27, 2023, and English translation thereof.
Search Report from corresponding Japanese Application No. 2021-513239 dated Jun. 30, 2023, and English translation thereof.

* cited by examiner

SAMPLE LOADING CARTRIDGE

TECHNICAL FIELD

The present invention generally relates to a sample loading cartridge, a device comprising such a sample loading cartridge and a method of loading a sample loading cartridge.

BACKGROUND

The recent development in single cell biology has made it clear that isogenic cells can display large differences in gene expression and behavior also when grown under identical conditions. New devices are thereby needed to characterize cell-to-cell differences in phenotypes over time. Such devices need to meet certain criteria in order to be an effective tool in culturing and monitoring single cells. For instance, these devices should be easy to load with cells so that one can monitor phenotypic characteristics immediately after loading. Furthermore, many different individual cells need to be grown in parallel to characterize the cell-to-cell differences and to overcome measurement errors in the characterization of individual cells by averaging. The devices should be designed to enable culturing of cells for a long period of time under constant and well-controlled growth conditions to monitor, for example, linage dependent dynamics. It is further preferred if the devices enable change of culturing conditions to monitor dynamic changes in response to new culture media or test agents. For instance, it could be advantageous to test different culture media on isogenic cells in parallel or monitor the response to media changes on different cell strains in parallel.

A desired application of microfluidic devices is to rapidly and in parallel monitor the phenotypic response of target cells, such as bacteria, in a biological sample to a set of antibiotics or other test agents immediately after the target cells have been loaded in the microfluidic device. In such an application, it would be advantageous to be able to directly load the microfluidic device with the biological sample to gain speed in the analysis. This could, for instance, be managed by connecting the microfluidic device to a sample loading cartridge, which can be pre-loaded with the biological sample and/or metered volumes of test agents.

A prior art microfluidic device, denoted the "Mother Machine", is disclosed in Wang et al., *Current Biology* 2010, 20: 1099-1103. The Mother Machine allows for monitoring cells in many different cell channels in parallel. However, this prior art microfluidic device has several shortcomings. For instance, cell loading is complicated and it is hard to rapidly change culture conditions in the microfluidic device.

Further microfluidic devices that are useful for analysis of biological samples are shown in WO 2016/007063 and WO 2016/007068.

Baltekin et al., *PNAS* 2017, 114(34): 9170-9175 discloses a fast antibiotic susceptible testing (AST) test, FASTest, using a microfluidic device.

Many microfluidic devices have shortcomings with regard to the accuracy and repeatability of loading specific volumes of samples or reagents into the microfluidic device in a simple way. There is therefore room for improvements to microfluidic devices in particular with regard to loading samples and reagents.

SUMMARY

It is a general objective to provide a sample loading cartridge having high accuracy and consistency with regard to loading specific volumes of samples or reagents into, for instance, microfluidic devices in a simple way.

This and other objectives are met by the embodiments disclosed herein.

The invention is defined in the independent claims. Further embodiments are defined in the dependent claims.

A sample loading cartridge for a microfluidic device of the invention comprises a cartridge body comprising a sample reservoir configured to house a volume of a liquid sample. The sample loading cartridge also comprises a sample port in connection with the sample reservoir and configured to receive the liquid sample. An output channel is connected to and extending from the sample reservoir, whereas a feedback channel is connected to the sample reservoir and to the sample port. The cartridge body comprises a detection portion aligned with at least a portion of the feedback channel to enable detection of presence of liquid sample in the feedback channel. According to the invention, a flow resistance of the feedback channel is lower than a flow resistance of the output channel to cause liquid sample received in the sample port to enter the feedback channel with substantially no liquid sample entering the output channel.

A device comprises a sample loading cartridge according to above and a microfluidic device in the form of a substrate comprising multiple cell channels having a respective first end in fluid connection with a flow input channel and a respective second end in fluid connection with a flow output channel. The cell channels comprise a respective channel restriction in connection with the respective second to prevent target cells entering the cell channels from reaching the flow output channel. The output channel of the sample loading cartridge is in fluid connection with the flow input channel.

A method of loading a sample loading cartridge comprises arranging a sample carrying device aligned with the sample port of a sample loading cartridge according to above. A liquid sample is transferred from the sample carrying device into the sample reservoir of the sample loading cartridge through the sample port until liquid sample is detectable in the feedback channel at the detection portion of the cartridge body.

The sample loading cartridge of the invention is designed to accurately and consistently load a metered volume of a liquid sample. Correct filling of the sample loading cartridge can be manually or automatically monitored and verified to ensure that the liquid sample has reached the flow output channel, and if needed to thereby obtain a correct volume of the liquid sample that may be transferred to downstream applications or appliances, such as to a microfluidic device. In particular, it is important to accurately determine the volume if reagents are mixed and/or dry reagents are dissolved in the sample loading cartridge.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present invention generally relates to sample loading cartridges and in particular to such sample loading cartridges that may be used to accurately and consistently load metered volumes of liquid samples for various applications and appliances, including into microfluidic devices.

Microfluidic devices are characterized by small dimensions of fluid channels, typically in the μm and nm range, and thereby minute volumes of liquid samples present in such microfluidic devices. Loading of accurately metered volumes of liquid samples in an efficient and simple way is not trivial due to the small dimensions and volumes, in particular when avoiding introduction of air or other driving fluids into the microfluidic devices. As a consequence, complex and cumbersome equipment is often required to accurately meter correct volumes of the liquid samples and then the equipment or another device is needed to load the metered volumes of the liquid samples into the microfluidic devices.

The sample loading cartridge of the invention enables accurate and consistent metering of volumes of liquid samples that may be transferred to various downstream applications and appliances, such as microfluidic devices. Correct filling of the sample loading cartridge of the invention can be easily monitored, detected or verified either manually or automatically using a detection equipment or instrument due to the presence of a feedback channel and due to the design of the feedback channel and an output channel of the sample loading cartridge.

Figure 1:
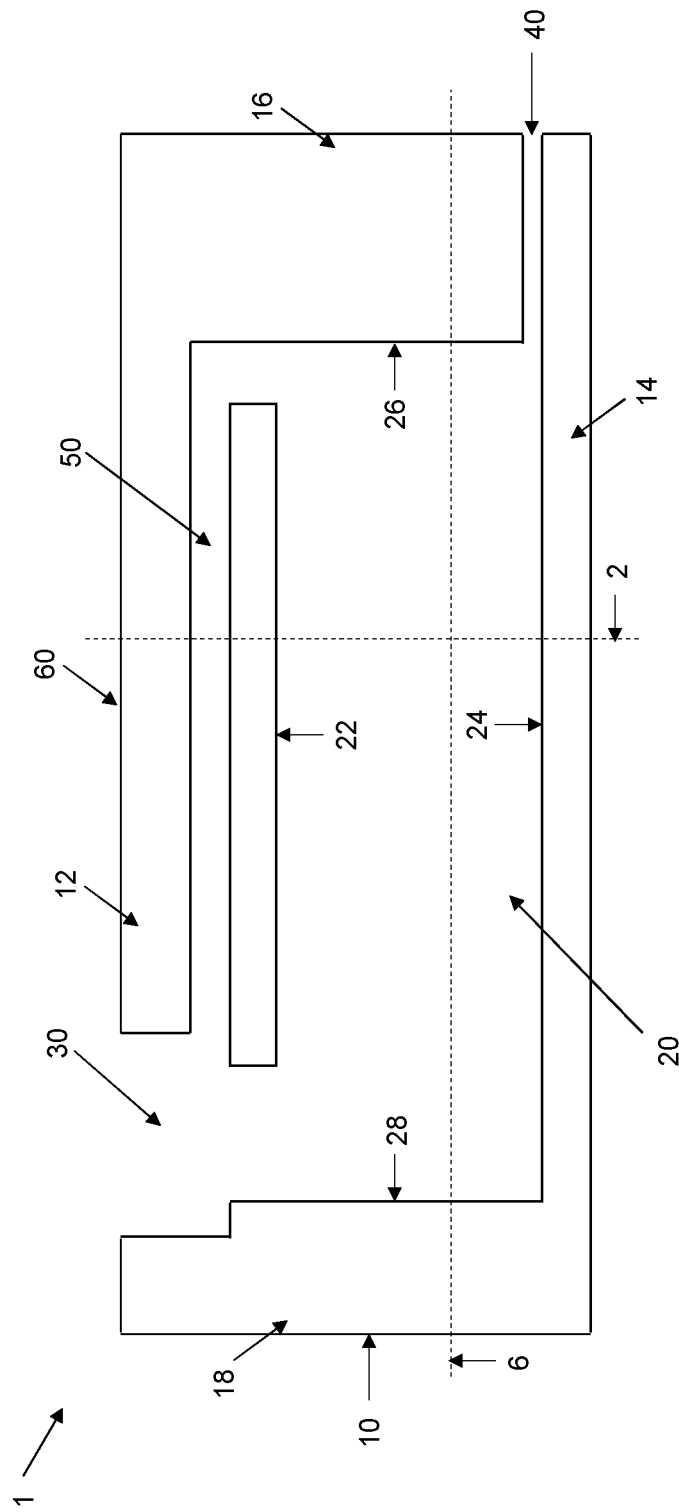
FIG. 1 illustrates a sample loading cartridge according to an embodiment.

FIG. 1 is a cross-sectional view of an embodiment of a sample loading cartridge 1 for a microfluidic device. The sample loading cartridge 1 comprises a cartridge body 10 comprising a sample reservoir 20 configured to house a volume of a liquid sample. A sample port 30 of the sample loading cartridge 1 is in connection, either directly as in FIG. 1 or indirectly as in FIG. 13, with the sample reservoir 20. The sample port 30 is configured to receive the liquid sample. An output channel 40 is connected to and extends from the sample reservoir 20. The sample loading cartridge 1 also comprises a feedback channel 50 connected to the sample reservoir 20 and connected, either directly as in FIG. 1 or indirectly as in FIG. 13, to the sample port 30. The cartridge body 10 comprises a detection portion 60 aligned with at least a portion of the feedback channel 50 to enable detection of presence of liquid sample in the feedback channel 50. The flow resistance of the feedback channel 50 is lower than the flow resistance of the output channel 40 to cause liquid sample received in the sample port 30 to enter the feedback channel 50 with substantially no liquid sample entering the output channel 40.

The sample loading cartridge 1 thereby comprises a sample reservoir 20 configured to be loaded with a liquid sample. The sample reservoir 20 may have any design, such as a cube, a rectangular cuboid or a cylinder as illustrative, but non-limiting, examples. The volume of the sample reservoir 20 defines the volume of the liquid sample that can be loaded into the sample loading cartridge 1.

The sample port 30 is in fluid, preferably liquid, connection with the sample reservoir 20 to enable filling of the sample reservoir 20 with liquid sample as entered through or at the sample port 30. In a particular embodiment, the sample port 30 is in the form of a port or opening in a ceiling 22 of the sample reservoir 20. In FIG. 1, this port or opening is provided in the ceiling 22 in connection with an end side 28 of the sample reservoir 20. Such a design is generally preferred to thereby allow entering of liquid sample into the sample reservoir 20 from one end, whereas the output channel 40 and the feedback channel 50 are preferably connected to the sample reservoir 20 at or in connection with an opposite end side 26 of the sample reservoir 20. The embodiments are, however, not limited thereto. For instance, the sample port 30 could be a port or opening in the ceiling 22 at any position from one of the end sides 26 to the opposite end side 28. It is also possible to have the sample port 30 connected to the sample reservoir 20 at one of the end sides 26, 28 or one of the longitudinal sides (not shown in FIG. 1) of the sample reservoir 20. In such a case, the sample port 30 is preferably, directly or indirectly, connected to the sample reservoir 20 through the side 26, 28 at the ceiling 22 or at a position close to the ceiling 22, such as high up in the side 26, 28 with regard to an axis 2 between the ceiling 22 and a bottom 24 of the sample reservoir 20.

The sample reservoir 20 could have any cross-sectional shape, such as circular, elliptical, quadratic or rectangular as illustrative, but non-limiting, examples.

The feedback channel 50 is preferably connected to the sample reservoir 20. For instance, the feedback channel 50 may extend from the sample reservoir 20, at the ceiling 22 as shown in FIG. 1. Alternatively, the feedback channel 50 may enter the sample reservoir 20 at any of the end sides 26, 28 or any of the longitudinal sides of the sample reservoir 20. In such a case, the feedback channel 50 preferably enters the sample reservoir 20 at the side 26, 28 at or close to the ceiling 22.

In a preferred embodiment, the sample port 30 is connected to the ceiling 22 of the sample reservoir 20 and the feedback channel 50 is connected to the ceiling 22 and to the sample port 30 as shown in FIG. 1.

The output channel 40 is connected to and extends from the sample reservoir 20 preferably at one of the sides 26, 28, such as one of the end sides 26, 28 or one of the longitudinal sides. In an embodiment, the output channel 40 is connected to and extends from one of the end sides 26, 28 of the sample reservoir 20, preferably from the end side 26 that is opposite to the end side 28 at which the sample port 30 is connected to the sample reservoir 20. Hence, in a preferred embodiment, the sample port 30 and the output channel 40 are preferably connected to the sample reservoir 20 at opposite end sides 26, 28 along an axis 6 running between these end sides 26, 28 of the sample reservoir 20 as shown in FIG. 1. In such a case, the feedback channel 50 preferably also enters the sample reservoir 20 at or in connection with the same end side 26 as the output channel 40.

The output channel 40 furthermore preferably enters the sample reservoir 20 at the side 26, 28, preferably the end side 26, at a position below the ceiling 22 with regard to an axis 2 extending between the bottom 24 and the ceiling 22 of the sample reservoir 20. This means that the entrance to the output channel 40 is preferably arranged below the entrance of the feedback channel 50 along the axis 2. For instance, the output channel 40 could extend from a side 26, 28 of the sample reservoir 20, preferably the end side 26, at or close to the bottom 24 of the sample reservoir 20.

Figure 2:
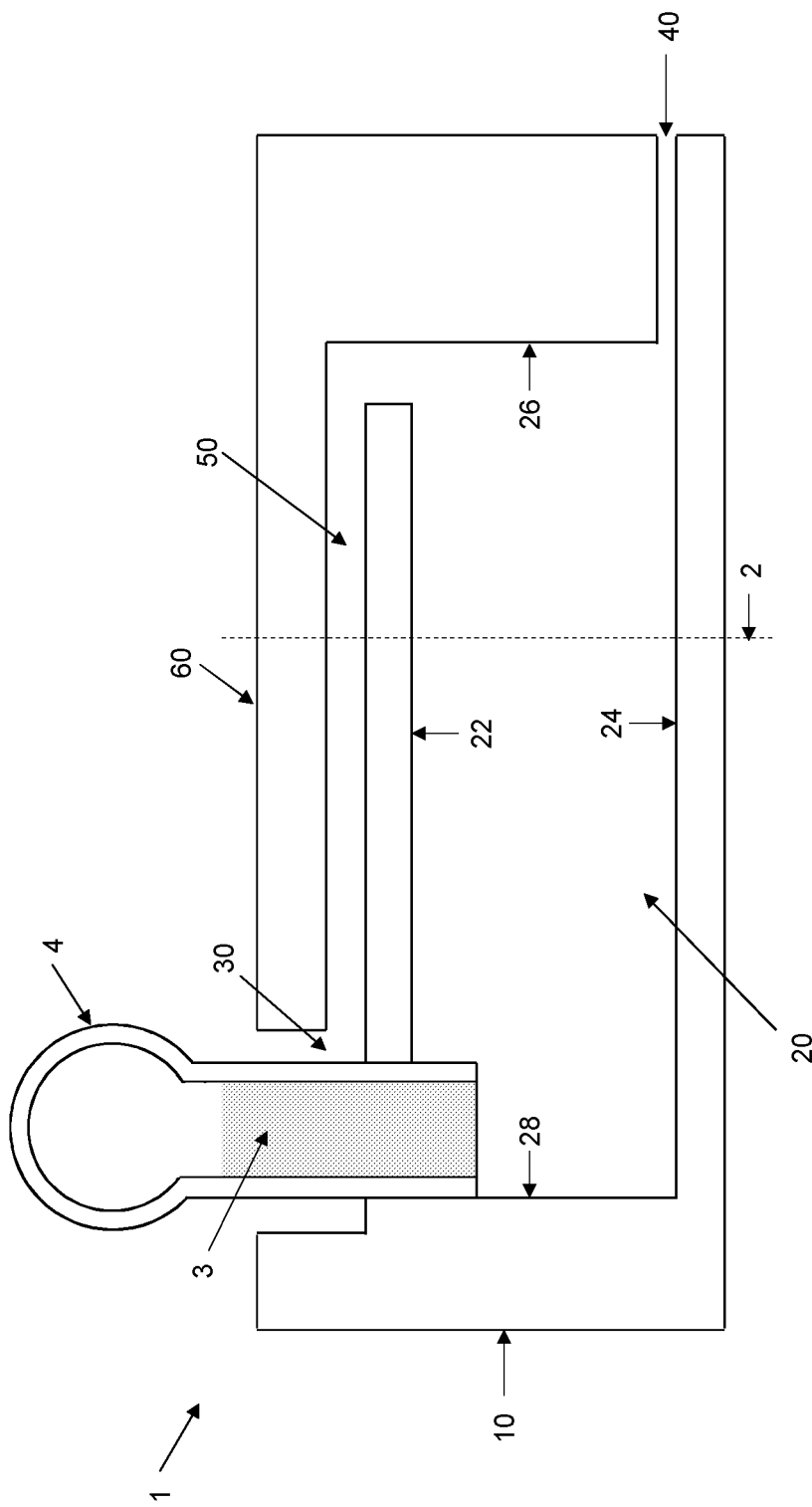
FIG. 2 illustrates the sample loading cartridge of FIG. 1 prior to sample loading.

FIG. 2 illustrates the sample loading cartridge 1 of FIG. 1, in which a sample carrying device 4 is aligned with, such as connected to, the sample port 30. The sample carrying device 4 could be any device that comprises a liquid sample 3 that is to be loaded into the sample reservoir 20 of the sample loading cartridge 1. For instance, the sample carrying device 4 could be a pipette, a syringe, a blister pack, a pre-filled sample chamber with connected pump as illustrative, but non-limiting, examples.

Depending on the dimensions of the sample reservoir 20, the filling thereof with the liquid sample 3 from the sample carrying device 4 can progress according to different embodiments.

In a first embodiment, the sample reservoir 20 has macrodimensions and thereby any flow resistance when filling the sample reservoir 20 is quite low. In such an embodiment, when the liquid sample 3 is transferred from the sample carrying device 4 into the sample reservoir 20 through the sample port 30 the liquid sample 3 starts to fill up the sample reservoir 20 from the bottom 24 up towards the ceiling 22. Air present in the sample reservoir 20 can escape through the feedback channel 50, which thereby also operates as an air vent, and optionally also through the output channel 40 depending on the flow resistance of the output channel 40.

Figure 3:
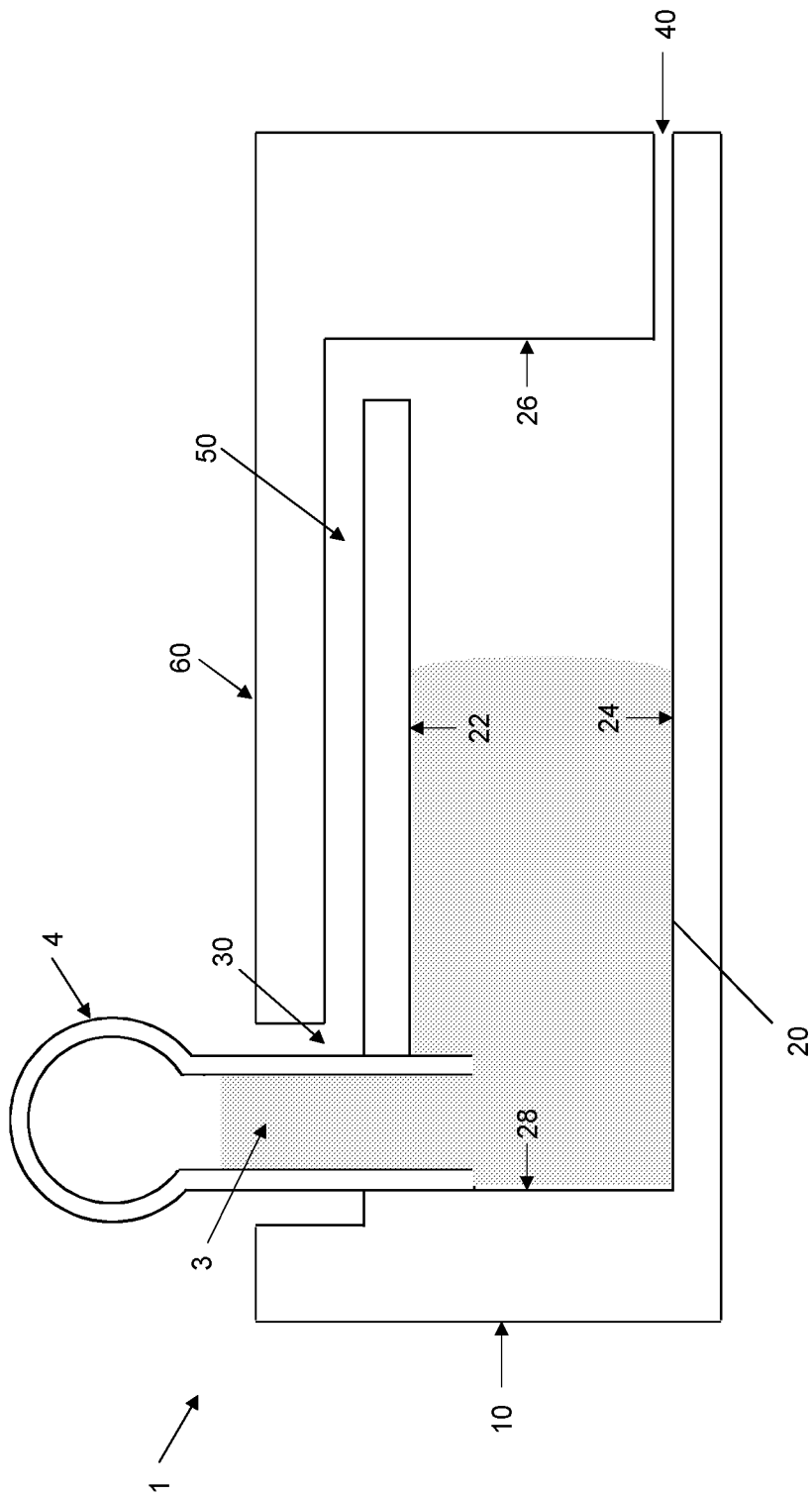
FIG. 3 illustrates the sample loading cartridge of FIG. 1 during sample loading.

FIG. 3 illustrates another embodiment during the filling of the sample reservoir 20. In this embodiment, the sample reservoir 20 typically has smaller dimensions and thereby presents a higher flow resistance to the liquid sample 3 transferred from the sample carrying device 4. In this embodiment, the sample reservoir 20 starts to fill up from one of its end sides 28, i.e., the end side 28 at which the sample port 30 is fluidly connected to the sample reservoir 20 in FIG. 3, and then progresses towards the opposite end side 26.

During the liquid sample filling, the high flow resistance of the output channel 40 prevents or restricts the liquid sample 3 from entering the output channel 40 during the filling phase. In clear contrast, the liquid sample 3 remains in and fills up the sample reservoir 20, while air is vented through feedback channel 50. At the point when the sample reservoir 20 is full with liquid sample 3, liquid sample 3 will enter the feedback channel 50. Thus, the comparatively higher flow resistance of the output channel 40 relative to the flow resistance of the feedback channel 50 causes liquid sample 3 to enter the feedback channel 50 when the sample reservoir 20 is full of fluid, such as the liquid sample 3, with substantially no liquid sample 3 entering the output channel 40.

In an embodiment, a ratio between the flow resistance of the feedback channel 50 and the flow resistance of the output channel 40 is less than $1/10$, preferably less than $1/100$ and more preferably less than $1/1000$.

In a typical embodiment, liquid sample 3 starts to enter the feedback channel 50 when the sample reservoir 3 is full of the liquid sample 3 with substantially no liquid sample 3 entering the output channel 40. In such an embodiment, the liquid sample 3 occupies the complete volume of the sample reservoir 20. In another embodiment, the sample reservoir 20 may be partly filled with the liquid sample 3 and then entering another fluid through the sample port 3 to push the liquid sample 3 into the feedback channel 50 with substantially no liquid sample 3 entering the output channel 40. In such an embodiment, the liquid sample 3 merely occupies a portion of the internal volume of the sample reservoir 20 with the added other fluid occupying the remaining part of the sample reservoir 20. This other fluid could be a gas, including a gas mixture, such as air. Another example of a fluid that could be used could be liquid that is insoluble in and does not mix with the liquid sample 3, such as an oil or oil-based liquid if the liquid sample 3 is water or an aqueous sample.

The flow resistance in the output channel 40 with regard to the liquid sample 3 is thereby significantly higher than the flow resistance in the feedback channel 50. The higher flow resistance of the output channel 40 as compared to the feedback channel 50 can be achieved by having a larger cross-sectional area of the feedback channel 50 as compared to the cross-sectional area of the output channel 40. For instance, the output channel 40 could have a diameter (in the case of a circular cross-sectional shape) or side (in the case of a quadratic or rectangular cross-sectional shape) within a range of from 1 μm up to 100 μm, preferably within a range of from 5 μm up to 75 μm, and more preferably within a range of from 10 μm up to 50 μm. Correspondingly, the feedback channel 50 may have a channel diameter or side within a range of from 250 μm up to 5 mm, preferably within a range of from 250 μm up to 1 mm, and more preferably within a range of from 250 μm up to 750 μm, such as about 500 μm.

In an embodiment, a ratio between the cross-sectional area of the output channel 40 and the cross-sectional area of the feedback channel 50 is preferably equal to or smaller than $1/50$, preferably equal to or smaller than $1/75$, and more preferably equal to or smaller than $1/100$.

The higher flow resistance of the output channel 40 as compared to the feedback channel 50 may also, or alternatively, be achieved by connecting the output channel 40 to a downstream microfluidic device having flow channels in the micrometer or nanometer range. In such a case, the fluid connection between the output channel 40 and the downstream microfluidic device or channel results in presenting a high flow resistance to the liquid sample 3 in the output channel 40 even if the dimension of the output channel 40 may be in the high micrometer range or even in the millimeter range. For instance, an output channel 40 having a diameter (in the case of a circular cross-sectional shape) or side (in the case of a quadratic or rectangular cross-sectional shape) above 100 µm, such as above 250 µm or even above 500 µm could be used.

Figure 4:
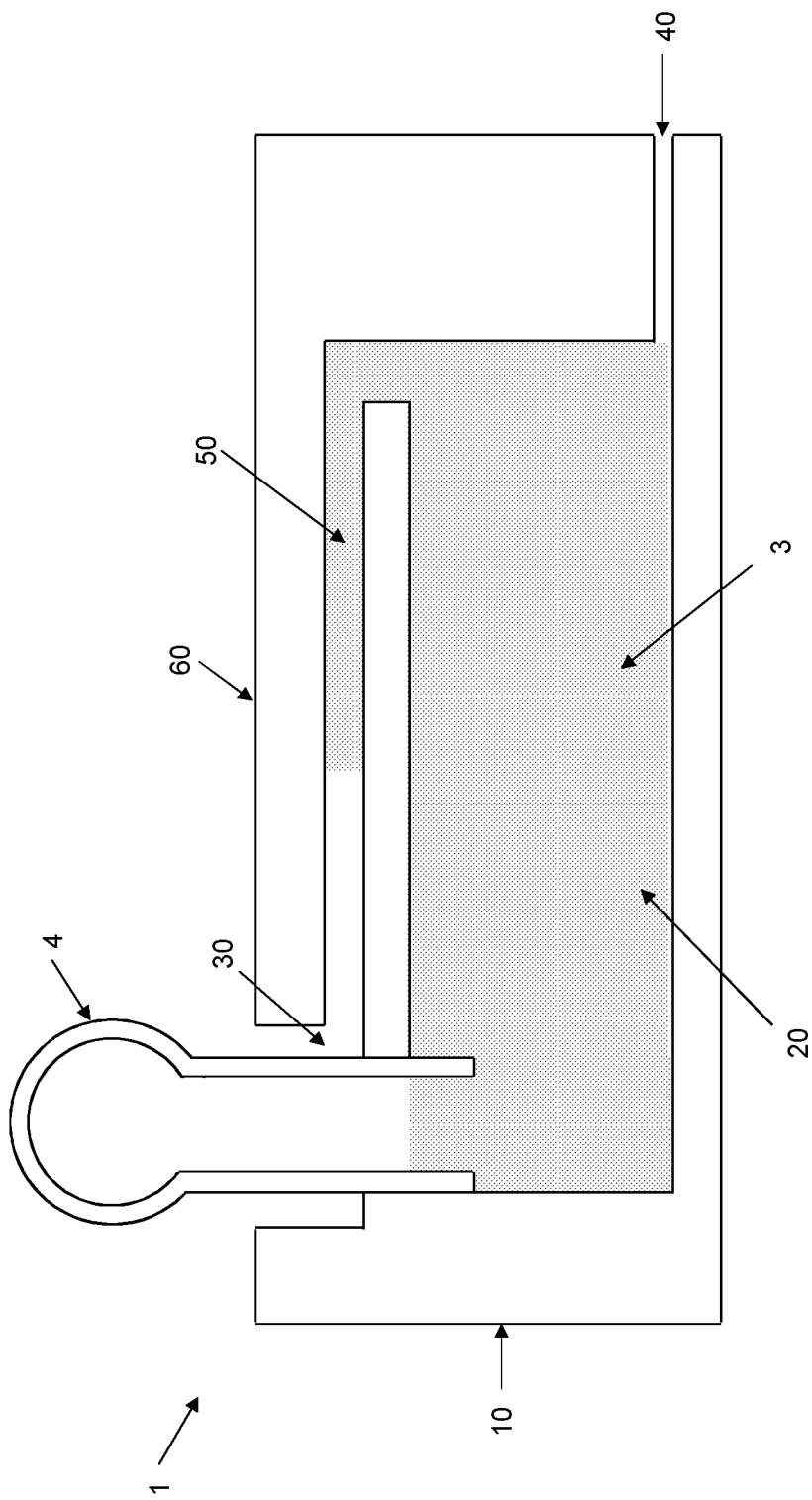
FIG. 4 illustrates the sample loading cartridge of FIG. 1 after sample loading.

FIG. 4 illustrates the sample loading cartridge 1 of FIG. 1 when the liquid sample 3 in the sample carrying device 4 has been transferred to the sample loading cartridge 1. As can be seen in the figure, the sample reservoir 20 is full with liquid sample 3 and therefore any further filling of liquid sample 3 into the sample reservoir 20 will cause liquid sample 3 to enter the feedback channel 50 with substantially no liquid sample 3 entering the output channel 40. When liquid sample 3 starts to fill the feedback channel 50, the liquid sample 3 can be detected at the detection portion 60 of the cartridge body 10 aligned with the feedback channel 50. Hence, detection of liquid sample 3 in the feedback channel 50 at the detection portion 60 verifies and confirms that the sample reservoir 20 has been filled with liquid sample 3 and any further filling can be stopped. The detection portion 60 thereby enables an efficient verification that the sample reservoir has been filled and that the sample reservoir 20 and, if applicable, the sample loading cartridge 1 thereby contains a correct volume of liquid sample 3.

Various implementation embodiments of the detection portion 60 are possible in order to monitor or detect and verify presence of liquid sample 3 in the feedback channel 50 and thereby correct filling of the sample reservoir 20. In an embodiment, the detection portion 60 comprises a window 60 aligned with the at least a portion of the feedback channel 50 to provide visual access to the feedback channel 50. This is more clearly seen in FIG. 5 showing a top view of the sample loading cartridge 1 of FIG. 4.

The window 60 could be in the form of a translucent or transparent window 60 to enable visual access to the at least a portion of the feedback channel 50. For instance, the window 60 could be made of a translucent or transparent material that is included in the cartridge body 10 aligned with the at least a portion of the feedback channel 50. This translucent or transparent material then enables visual access to the feedback channel 50, or at least a portion thereof, even if the other parts 12, 14, 16, 18 of the cartridge body 10 are made of an opaque material. In another embodiment, the whole sample loading cartridge 1, or at least the top part 12 thereof, is made of a translucent or transparent material to allow access into the feedback channel 50. Another solution is to have a window 60 in the form of an opening or recess in the top part 12 of the cartridge body 10 aligned with the at least a portion of the feedback channel 50. In such a case, visual access to the feedback channel 50 is possible through the opening or recess. The feedback channel 50 is thereby an at least partly open channel in the cartridge body 10.

Figure 5:
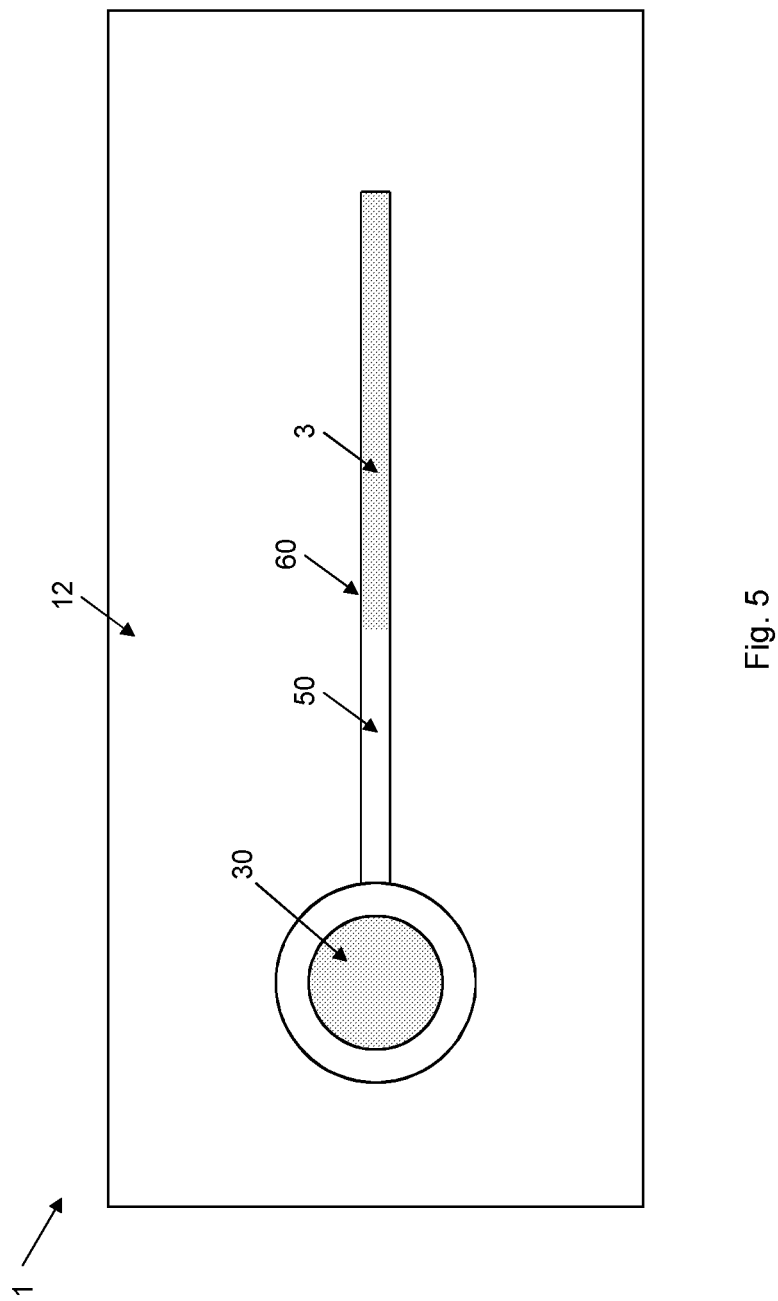
FIG. 5 illustrates the sample loading cartridge of FIG. 4 as seen from above.

The window 60 could extend along the whole length of the feedback channel 50 as shown in FIG. 5. In another embodiment, the window 60 extends along only a portion of the feedback channel 50, such as a portion in connection with the entrance of the feedback channel 50 into the sample reservoir 20, a portion in connection with the exit of the feedback channel 50 into the sample port 30 or an intermediate portion of the feedback channel 50. The window 60 could be in the form of a single, possibly extended, window 60. Another possibility is to have several separate windows 60 extending along different portions of the feedback channel 50.

In the above disclosed embodiments, presence of liquid sample 3 in the feedback channel 50 and thereby correct filling of the sample reservoir 20 can be detected visually, such as by a human operator. The human operator thereby gets direct visual feedback when sufficient liquid sample 3 has been transferred into the sample loading cartridge 1 and the sample reservoir 20.

The window-based embodiment also enables an automatic detection of presence of liquid sample 3 in the feedback channel 50 and thereby correct filling of the sample reservoir 20. For instance, a camera or other optical instrument could monitor the window 60 to detect any liquid sample 3 there through. The camera or instrument could then generate a signal, such as visual signal or audible signal, once liquid sample 3 is detected in the feedback channel 50 through the window 60. This signal instructs the human operator to stop the filling of the sample loading cartridge 1 as the sample reservoir 20 is already full. It is, in fact, also possible to have a controlled filling of liquid sample 3 from the sample carrying device 4 and where the filling is controlled, such as stopped, based on the signal generated by the camera or instrument. Thus, once the camera or instrument detects liquid sample 3 in the feedback channel 50 through the window 60 it generates and transmits the signal to a pump or other equipment of or connected to the sample carrying device 4 to thereby cause the pump or other equipment to stop the transfer of liquid sample 3 from the sample carrying device 4 into the sample reservoir 20.

Figure 9:
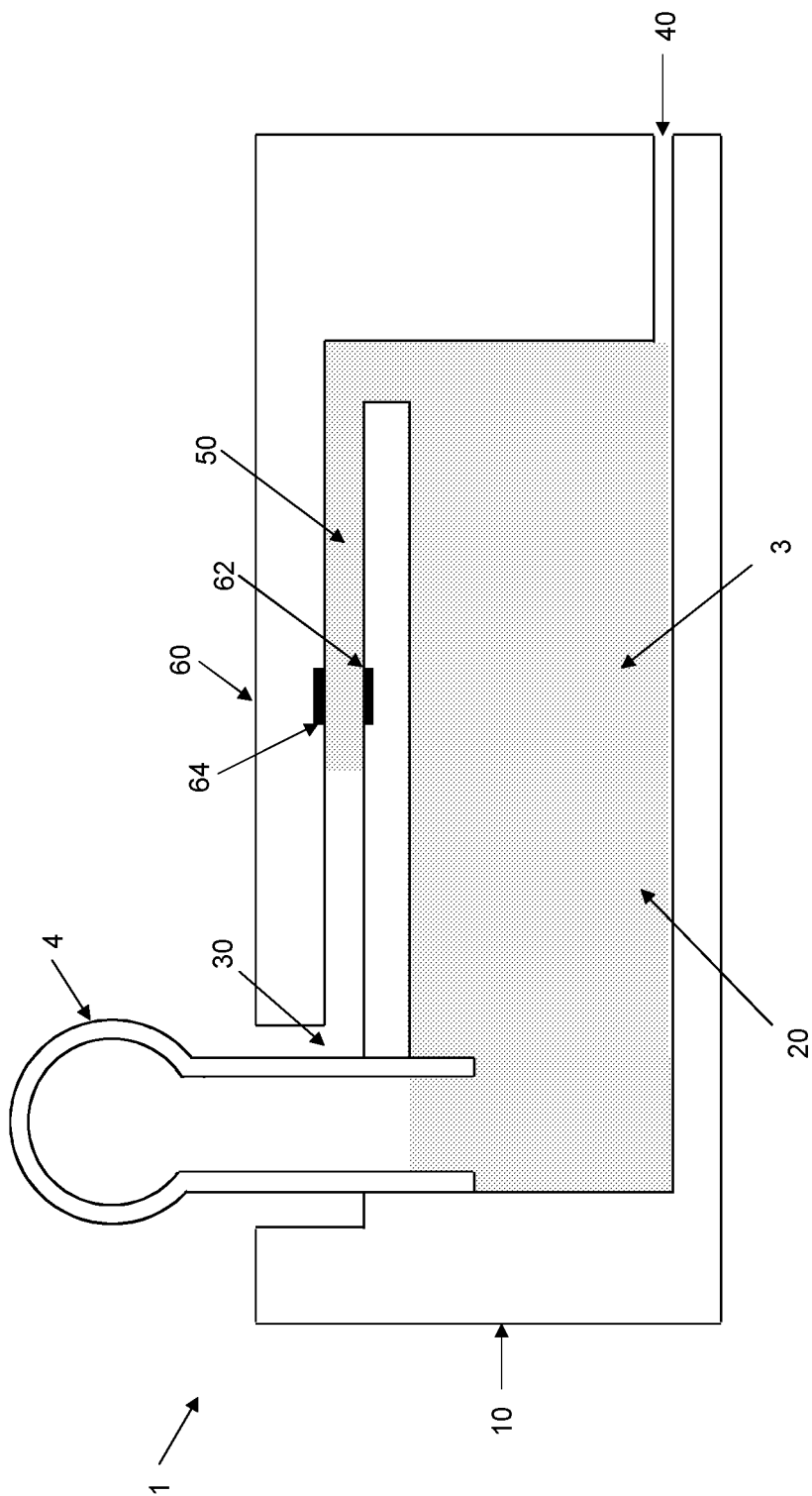
FIG. 9 illustrates a sample loading cartridge according to another embodiment.

FIG. 9 is an illustration of a sample loading cartridge 1 using another technique of detecting presence of liquid sample 3 in the feedback channel 50. This alternative technique could be used instead of or as complement to the window-based solution described in the foregoing. In the embodiment shown in FIG. 9, the detection portion 60 comprises at least one electrode 62, 64, two such electrodes 62, 64 are shown in the figure, arranged to measure, for instance, a current between the at least two electrodes 62, 64. In this embodiment, the liquid sample 3 is electrically conductive. Thus, when the liquid sample 3 enters the feedback channel 50 and electrically interconnects the at least two electrodes 62, 64 presence of liquid sample 3 in the feedback channel 50 can be verified by measuring the current between the at least two electrodes 62, 64.

In FIG. 9, the two electrodes 62, 64 are arranged in the ceiling and the bottom of the feedback channel 50 and are thereby configured to measure the current across the feedback channel 50. Another solution could be to arrange the two electrodes 62, 64 on respective longitudinal sides (not shown in FIG. 9) of the feedback channel 50 to also measure the current across the feedback channel 50. Further alternatives include arranging one of the electrodes 62, 64 at the ceiling or bottom of the feedback channel 50 and the other electrode 64, 62 at one of the longitudinal sides or arranging both electrodes 62, 64 at the ceiling, at the bottom or at one of the longitudinal sides of the feedback channel 50.

It is also possible to have one of the electrodes 62 arranged in the feedback channel 50 with the other electrode 64 arranged elsewhere in cartridge body 10 to form an electrical circuit between the electrodes 62, 64 and the liquid sample 3. For instance, the other electrode 64 could be arranged in the sample reservoir 20.

Instead of measuring the current between the two electrodes 62, 64 other electric properties could be measured or monitored, such as capacitance, resistance, frequency or voltage, in order to detect presence of liquid sample 3 in the feedback channel 50. In such a case, presence of liquid sample 3 between the two electrodes 62, 64 causes a change in capacitance, resistance, frequency or voltage and where such a change is a verification of the presence of liquid sample 3 in the feedback channel 50.

The two electrodes 62, 64 could be point-like electrodes or flat electrodes extending over an area. The detection portion 60 could include one pair of electrodes 62, 64 or multiple, i.e., at least two, pairs of electrodes 62, 64. In the latter case, the pairs of electrodes 62, 64 could be distributed along the feedback channel 50 and thereby arranged at different positions along the length of the feedback channel 50.

Figure 10:
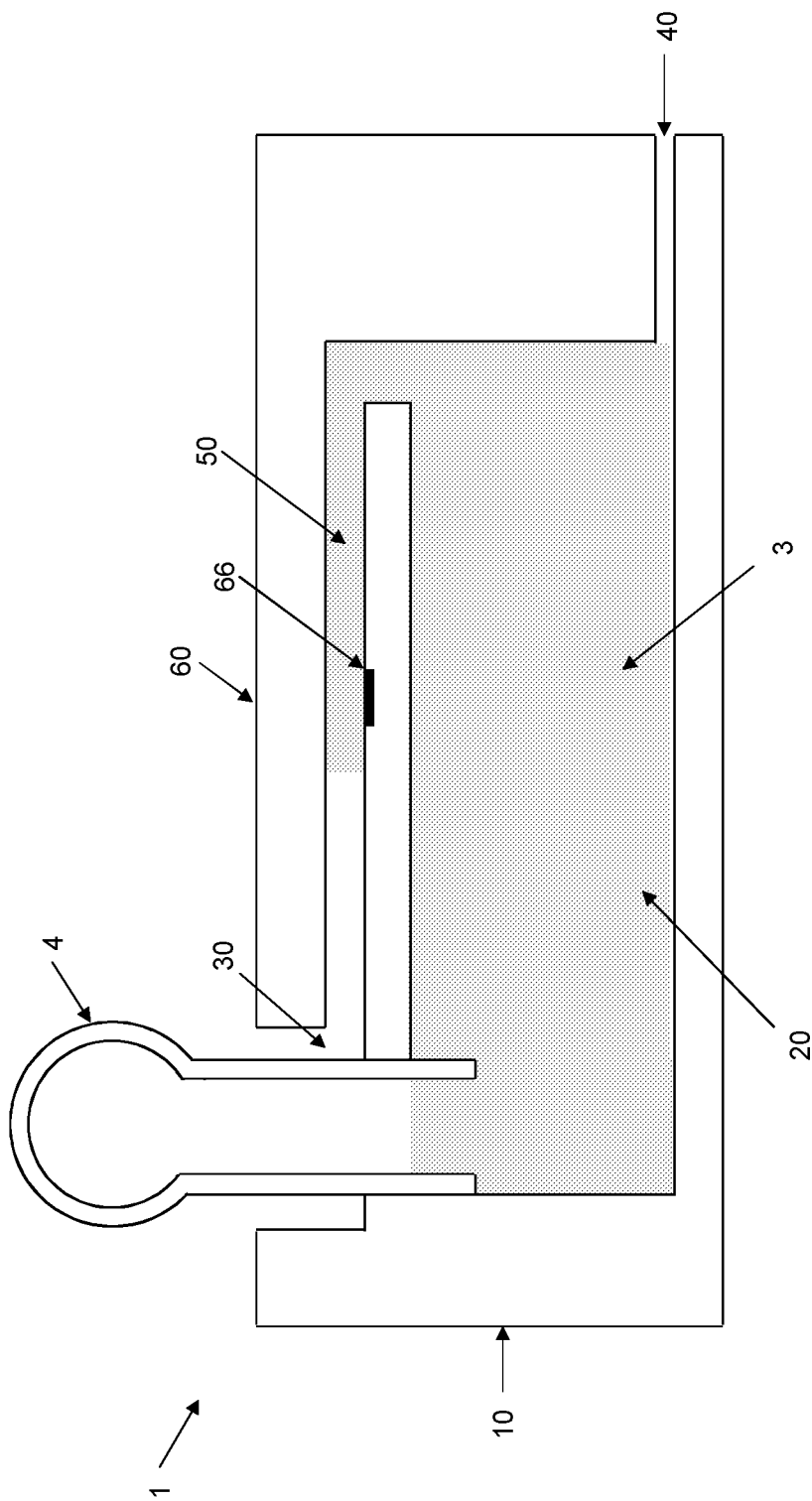
FIG. 10 illustrates a sample loading cartridge according to a further embodiment.

In a further embodiment, the detection portion 60 includes a sensor 66 configured to detect presence of liquid sample 3 in the at least a portion of the feedback channel 50, see FIG. 10. Various sensors 66 could be used to detect presence of liquid sample 3 in the feedback channel 50. For instance, the sensor 66 could be a piezoelectric sensor 66 arranged in the ceiling, bottom and/or a longitudinal side of the feedback channel 50, preferably a bottom of the feedback channel 50. In such a case, when liquid sample 3 contacts the piezoelectric sensor 66, the sensor 66 generates an electric signal indicative of presence of liquid sample 3 in the feedback channel 50 and thereby a correct filling of the sample reservoir 20. Other sensor examples include temperature sensors, pressure sensors, magnetic sensors, optical sensors, such as fluorescent sensors or chemiluminescent sensors.

As with the electrode-based embodiment above, one sensor 66 could be arranged anywhere along the length of the feedback channel 50 or multiple sensors 66 could be arranged at different positions along the length of the feedback channel 50.

The examples of generating a signal upon detection of liquid sample 3 in the feedback channel 50 and/or automatically stopping further filling of liquid sample 3 into the sample reservoir 20 from the sample carrying device 4 described above in connection with the window-based embodiment can also be used in connection with the electrode-based and sensor-based embodiments.

In some embodiments, the sample loading cartridge 1 could be pre-loaded with one or more reagents, preferably in the sample reservoir 20, which are dissolved in and/or mixed with the liquid sample 3 upon addition of the liquid sample 3 to the sample reservoir 20. In these cases, the window, electrode(s) or sensor in the detection portion 60 of the feedback channel 50 could be used to verify the concentration of the reagent in the liquid sample 3. This could for example be performed by visual inspection if the reagent contains a dye or a fluorophore, but it could for example also be done by electrical sensing if the reagent modifies the electrochemical properties of the liquid sample 3.

The sample loading cartridge 1 could be pre-loaded with liquid sample 3 in the sample reservoir 20 as described above. The sample loading cartridge 1 can then be stored with the liquid sample 3 for some time prior to transferring the liquid sample 3 from the sample loading cartridge 1 and the sample reservoir 20 to some downstream application or appliance, such as a microfluidic device. Alternatively, the sample loading cartridge 1 could, once its sample reservoir 20 has been filled with liquid sample 3, be used substantially directly to transfer liquid sample 3 to the downstream application or appliance.

Figure 6:
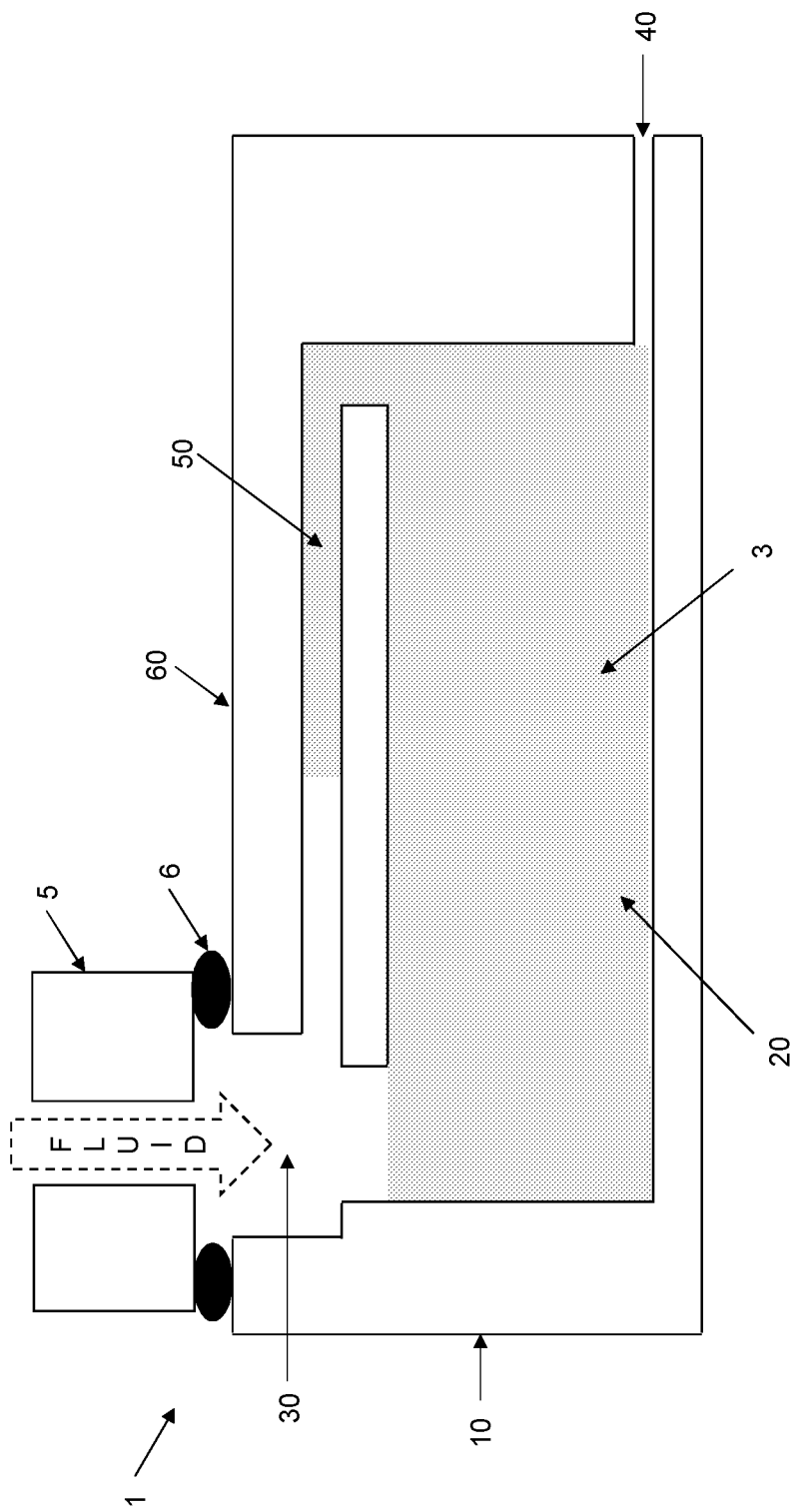
FIG. 6 illustrates the sample loading cartridge of FIG. 1 prior to sample ejection.

FIG. 6 schematically illustrates the sample loading cartridge of FIG. 1 prior to sample ejection. In FIG. 6, a fluid flow circuitry 5 is sealingly connected to the sample port 30. "Sealingly connected" as used herein indicates that there is a fluid tight or substantially fluid tight connection between the fluid flow circuitry 5 and the sample loading cartridge 1. The fluid flow circuitry 5 thereby comprises a seal 6, such as in the form of an O-ring, proving a fluid tight seal between the fluid flow circuitry 5 and the sample loading cartridge 1, such as between the fluid flow circuitry 5 and the top part 12 of the cartridge body 10.

Figure 7:
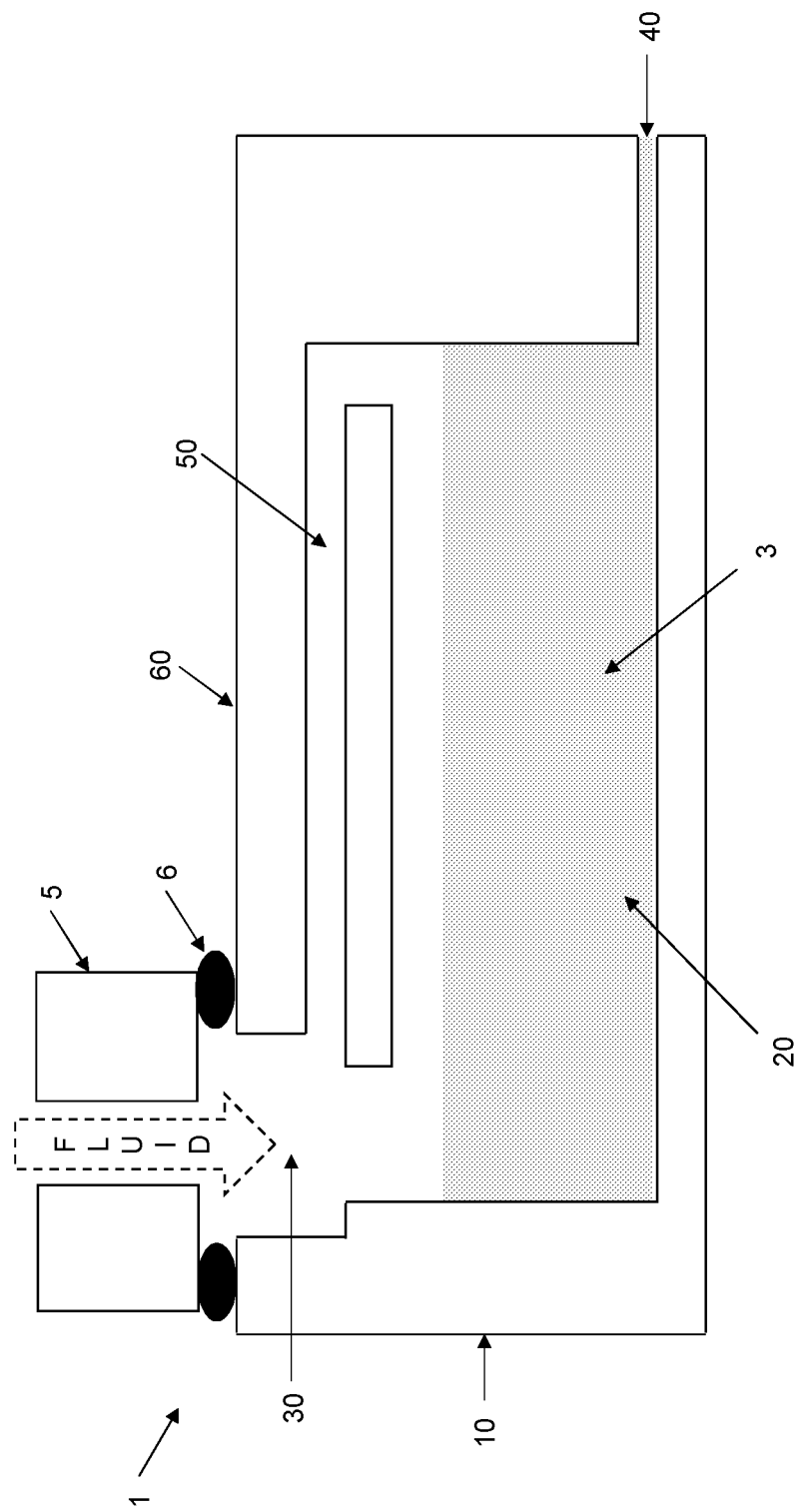
FIG. 7 illustrates the sample loading cartridge of FIG. 1 during sample ejection according to an embodiment.
Figure 8:
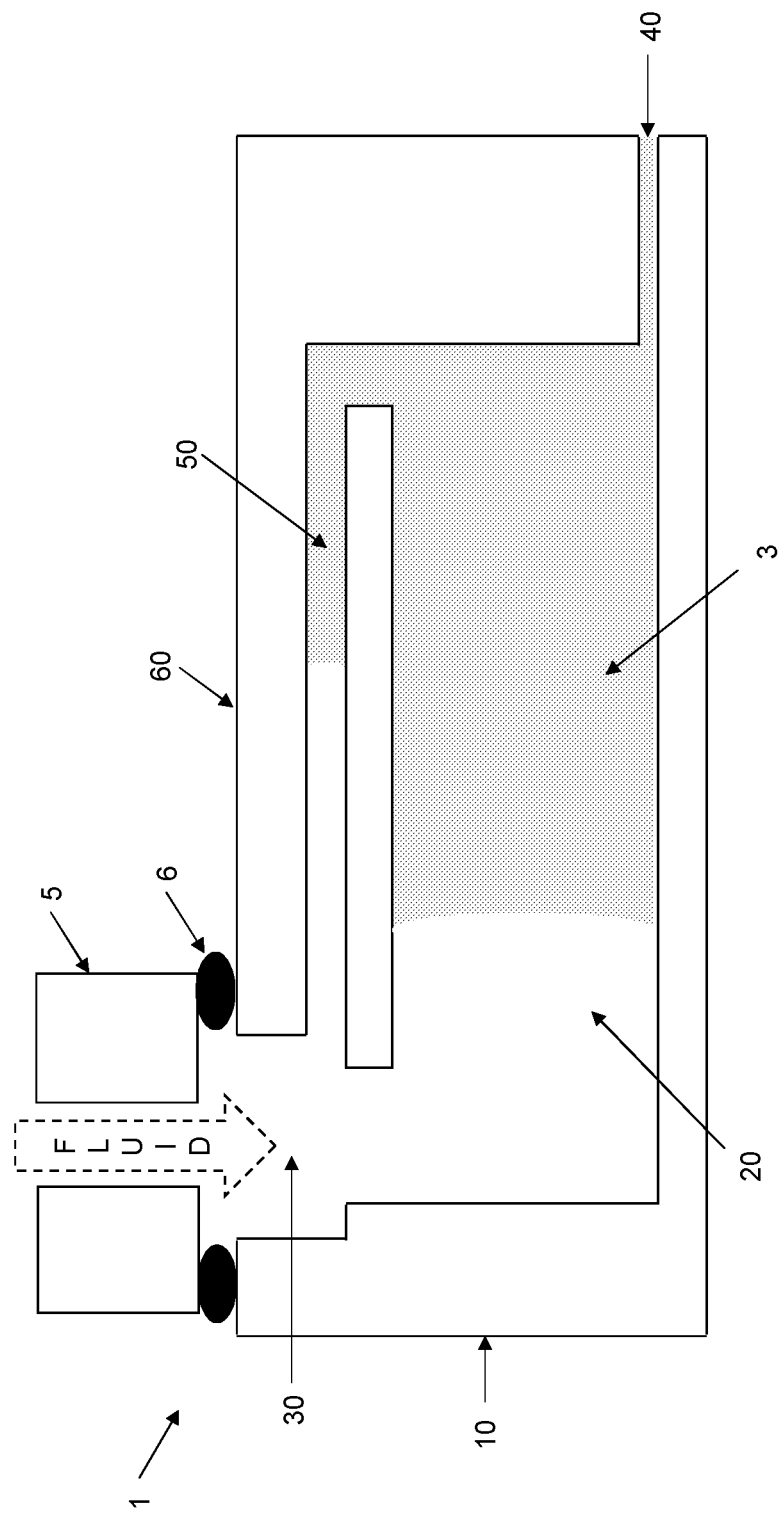
FIG. 8 illustrates the sample loading cartridge of FIG. 1 during sample ejection according to another embodiment.

The fluid flow circuitry 5 is arranged to provide a fluid flow into the sample port 30 as indicated by the hatched arrow in FIG. 6. The fluid flow then ejects liquid sample 3 in the sample reservoir 20 out through the output channel 40 as shown in FIG. 7 or 8 depending on the dimensions of the sample reservoir 20 and the feedback channel 50, or more correctly, depending on the flow resistance during the ejection phase. Hence, FIG. 7 illustrates sample ejection with a sample reservoir 20 in macrodimensions with FIG. 8 showing sample ejection with a sample reservoir 20 in microdimensions.

The fluid flow circuitry 5 could be any circuitry capable of generating a fluid flow of sufficient pressure to eject liquid sample 3 through the output channel 40 having a comparatively higher flow resistance. Non-limiting example of such fluid flow circuitry 5 that could be used include flow control valves and regulators by Festo, such as VEMP, VEAA, VEAB, VPCF, VPPX, VPPM, VPPM-NPT, VPWP, MPPES, VPPE, MPYE and VPPL. Generally, the liquid sample 3 could be ejected from the sample reservoir 20 using pressure and/or a fluid flow from any unit or circuitry 5. The fluid flow circuitry 5 could be a regulated fluid flow circuitry 5, in which the fluid flow could be controlled. The embodiments are, however, not limited thereto. For instance, the fluid flow circuitry 5 could be pressurized fluid chamber that does not necessarily have a fluid flow control.

Instead of, or as a complement to, ejecting the liquid sample 3 from the sample reservoir 20 by providing a fluid flow at the sample port 30, a negative pressure can be applied at the output channel to thereby "suck" the liquid sample 3 through the output channel 40.

The fluid in the fluid flow provided by the fluid flow circuitry 5 could be any gas, gas mixture or liquid compatible with the liquid sample 3. An illustrative, but non-limiting, example of such a gas is air.

In a further embodiment, a flexible membrane (not shown) could be arranged at and covering the sample port 30. In such a case, a flow of the liquid sample 3 out through the output channel 40 could be induced by applying a fluid or mechanical pressure onto the flexible membrane. In such a case, the interior of the cartridge body 10 will be isolated from the equipment generating the flow-driving pressure and the risk for any contamination of the equipment by the liquid sample 3 is minimized.

Figure 11:
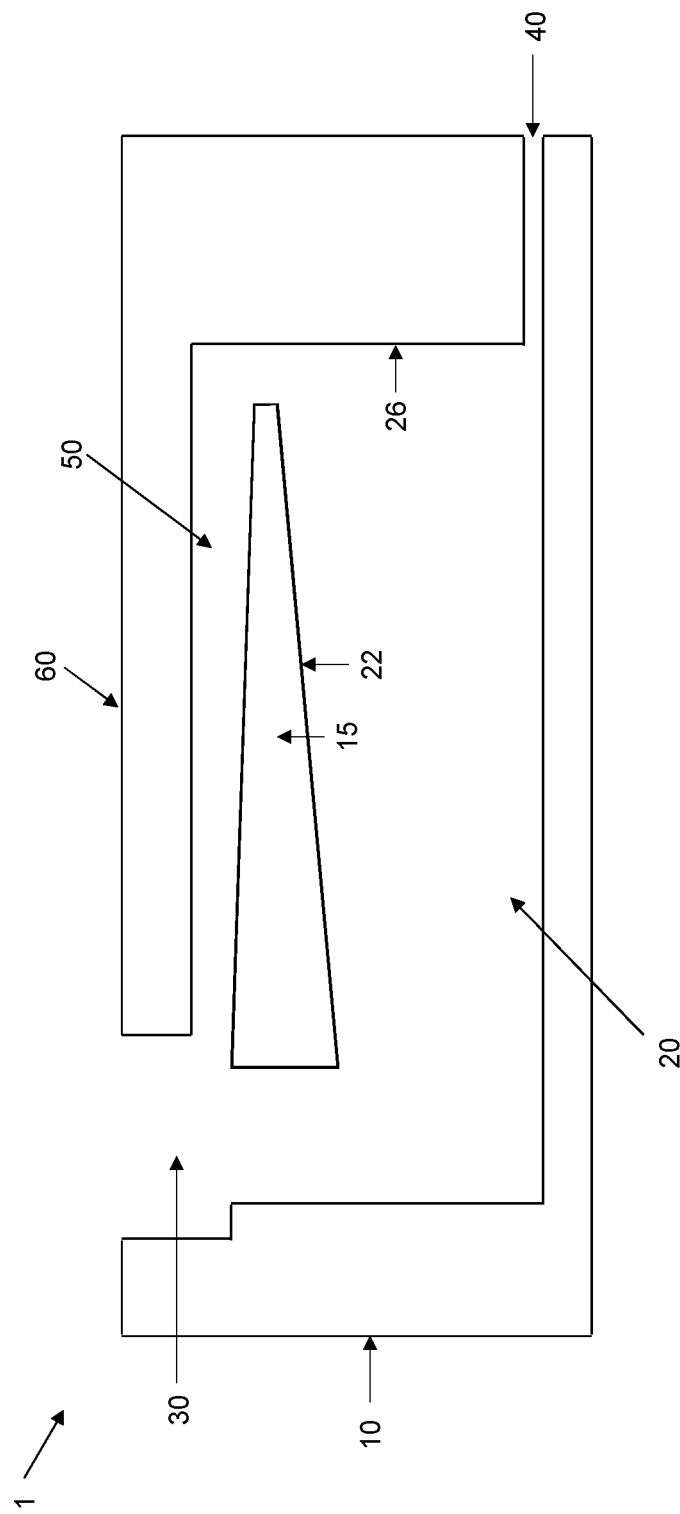
FIG. 11 illustrates a sample loading cartridge according to yet another embodiment.
Figure 12:
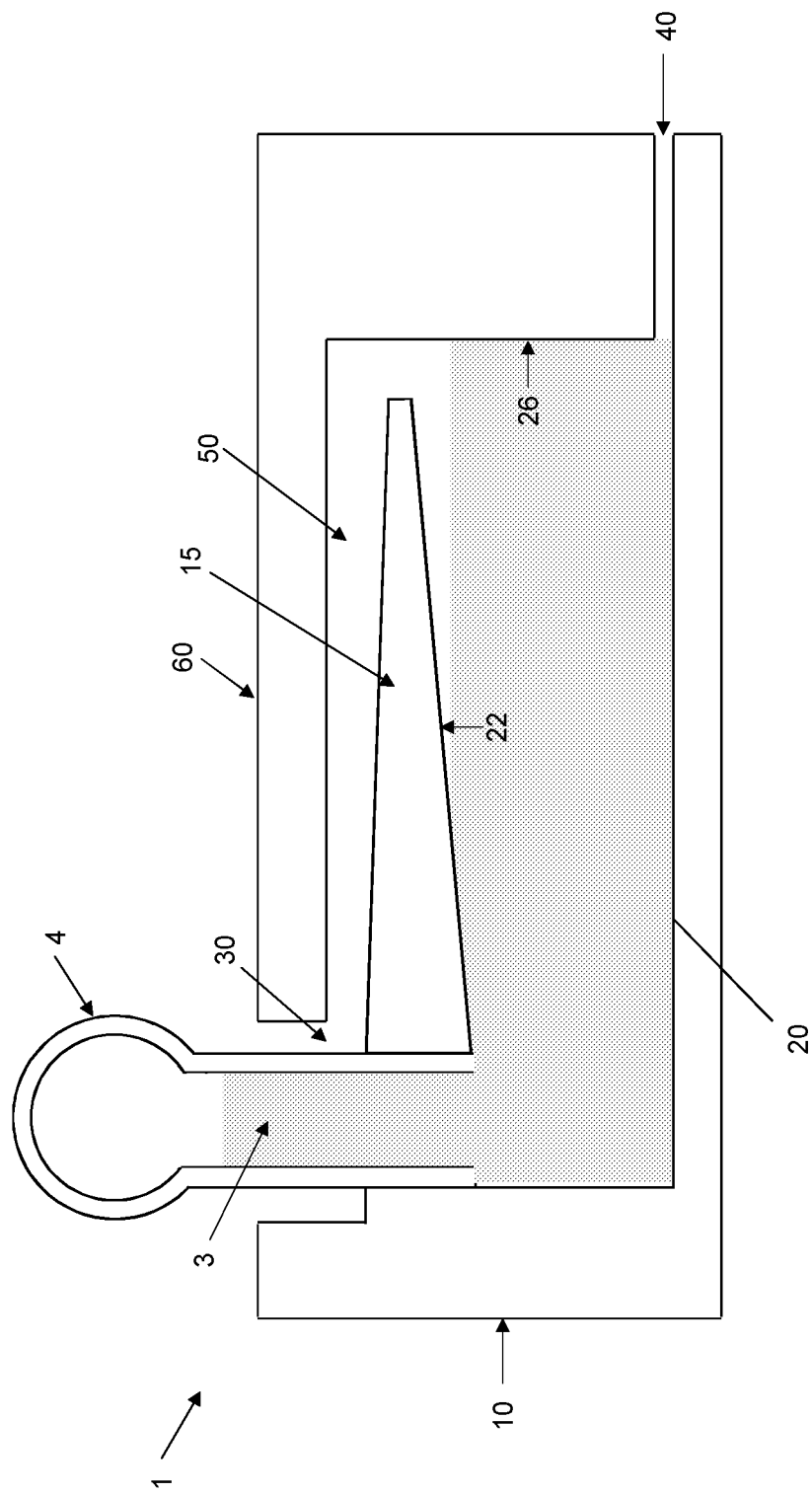
FIG. 12 illustrates the sample loading cartridge of FIG. 11 during sample loading.

FIGS. 11 and 12 illustrate another embodiment of the sample loading cartridge 1. In this embodiment, the structure 15 of the cartridge body 10 constituting the ceiling 22 of the sample reservoir 20 and the bottom of the feedback channel 50 may be wedge shaped. In such a case, the thickness of this structure 15 is smaller at the end facing the end side 26 as compared to the thickness at the end facing the sample port 30. In an embodiment, the structure 15 is in the form of a single wedge, i.e., having one substantially flat surface and one sloping surface. For instance, the bottom of this structure 15, i.e., the ceiling 22 of the sample reservoir 20, could be sloping with the top of the structure 15 constituting the bottom the feedback channel 50 is flat. Alternatively, the bottom of the structure 15 could be flat with the top of the structure could be sloping. In another embodiment, the structure 15 is in the form of a double wedge as shown in FIG. 11 having sloping top and bottom.

Having a wedge shaped structure 15 separating the sample reservoir 20 and the feedback channel 50 facilitates venting air out through the feedback channel 50 during filling of the sample reservoir as shown in FIG. 12.

Figure 13:
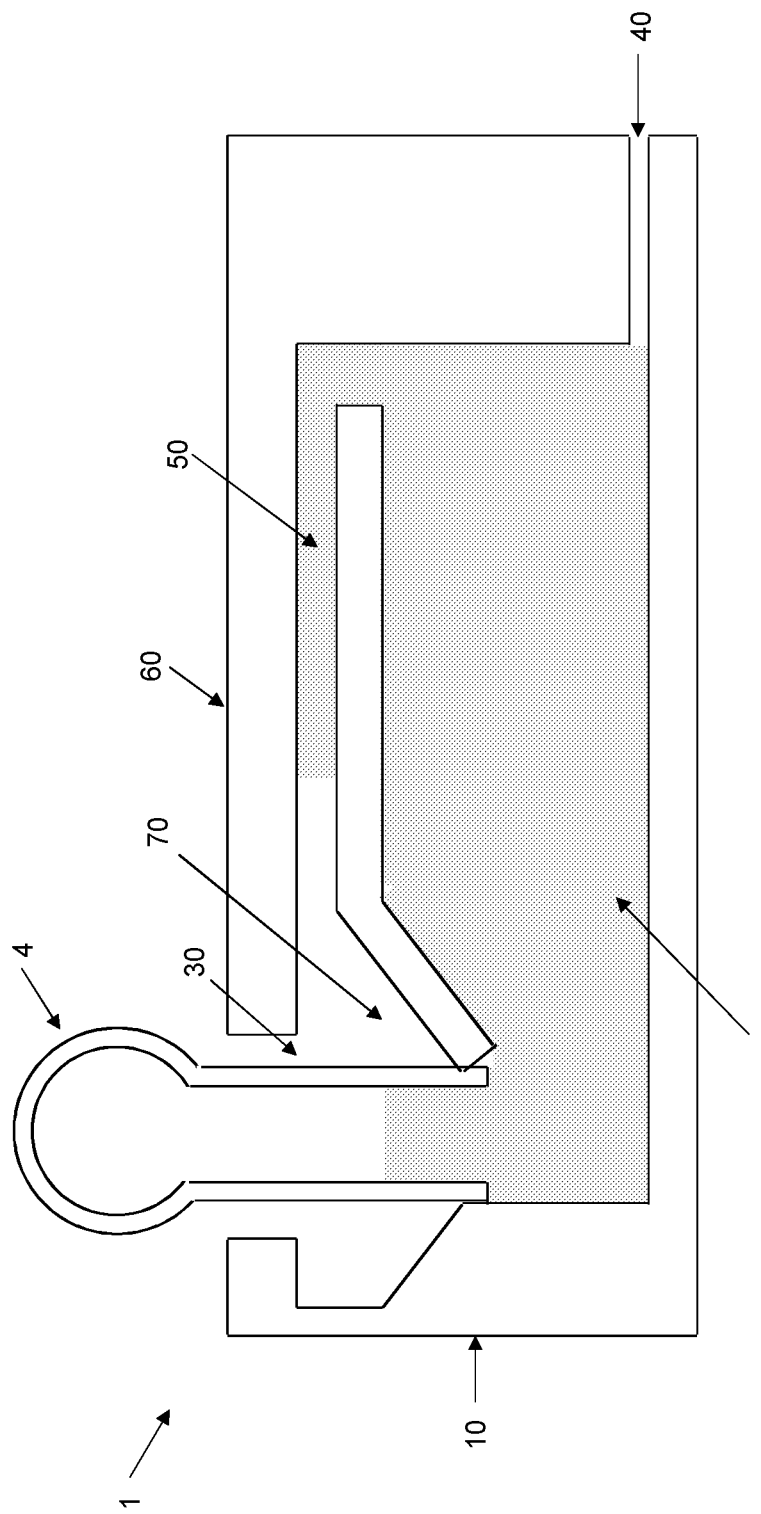
FIG. 13 illustrates a sample loading cartridge according to a further embodiment.

FIG. 13 illustrates another embodiment of the sample loading cartridge 1. In this embodiment, the sample loading cartridge 1 comprises an overfill reservoir 70 interposed between the sample port 30 and the sample reservoir 20. The feedback channel 50 is, in this embodiment, connected to the sample reservoir 20 and to the overfill reservoir 70. Hence, in this embodiment, the feedback channel 50 is in fluid connection with, but physically in indirect connection with, the sample port 30 through the overfill reservoir 70. Having an overfill reservoir 70 interposed between the sample port 30 and the sample reservoir 20 as shown in FIG. 13 reduces the risk of overfilling the sample loading cartridge 1 with liquid sample 3. Thus, if the sample reservoir 20 is filled with liquid sample 3 and the feedback channel 50 starts to fill with liquid sample 3, any excess liquid sample 3 will enter the overfill reservoir 70 and remain therein. Hence, the risk of overfilling the sample loading cartridge 1 causing excess liquid sample 3 to escape out through the sample port 30 is thereby reduced. Hence, the overfill reservoir 70 lowers the risk of contaminating the sample loading cartridge 1 and in particular the top part 12 of the cartridge body 10 with liquid sample 3 during the sample loading phase.

Figure 14:
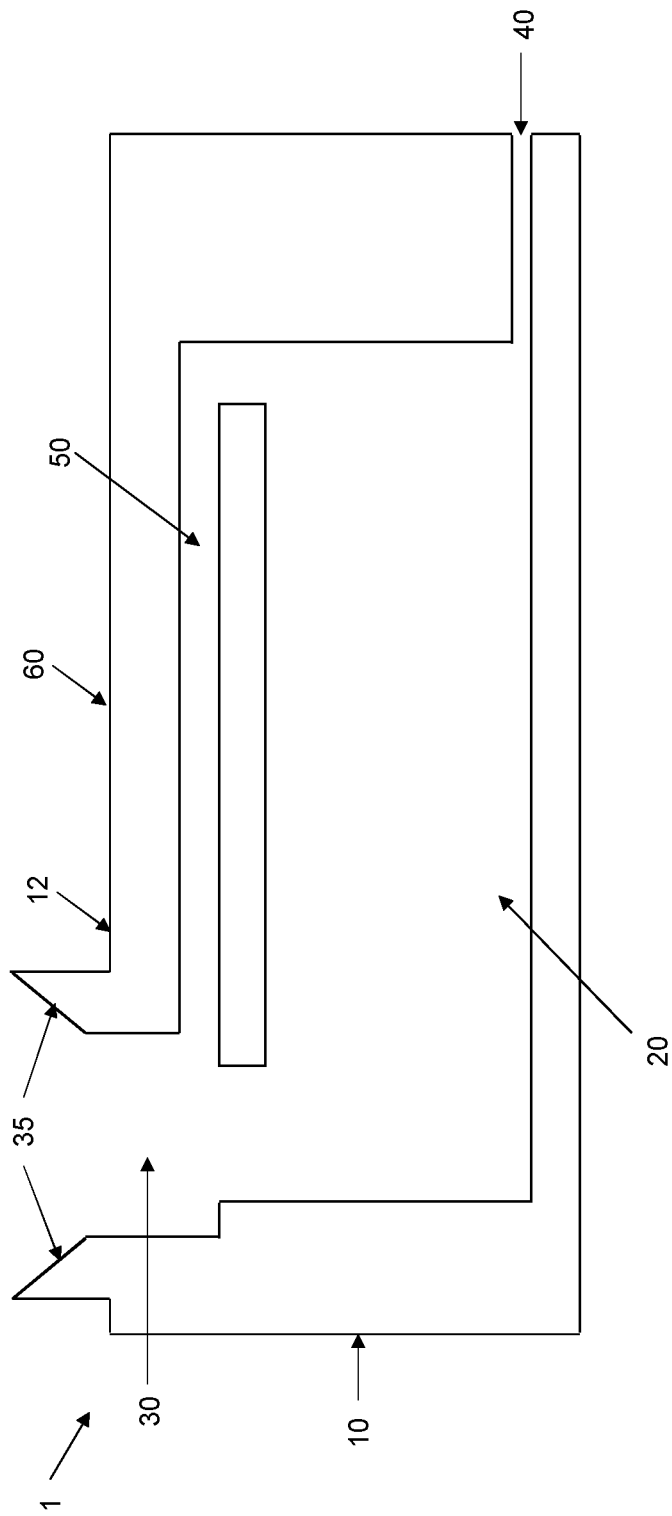
FIG. 14 illustrates a sample loading cartridge according to yet another embodiment.

Another embodiment of the sample loading cartridge 1 with reduced risk of overfilling and contamination is shown in FIG. 14. In this embodiment, the sample port 30 comprises a funnel-shaped structure 35. The funnel-shaped structure 35 may extend from the cartridge body 10 as shown in FIG. 14. The funnel-shaped structure 35 is advantageously circumferentially arranged around the sample port 30, thereby forming an extending, with regard to the top part 12 of the cartridge body 10, structure providing a funnel-shaped opening into the sample port 30. Any excess liquid sample 3 escaping the feedback channel 50 and/or the sample reservoir 20 during the loading phase will then be contained in the extra volume defined by the funnel-shaped structure 35.

In another embodiment, the funnel-shaped structure 35 is present in the cartridge body 10 and does not necessary extend from the cartridge body 10 and above the top part 12 of the cartridge body 10. This means that the sample port 30 is preferably in the form of a funnel-shaped structure 35.

The embodiments shown in FIGS. 13 and 14 can be combined. Hence, the sample loading cartridge 1 may comprise an overfill reservoir 70 as shown in FIG. 13 and a funnel-shaped structure 35 as shown in FIG. 14. Furthermore, any of such embodiments could include a wedge shaped structure 15 as shown in FIGS. 11 and 12.

Figure 15:
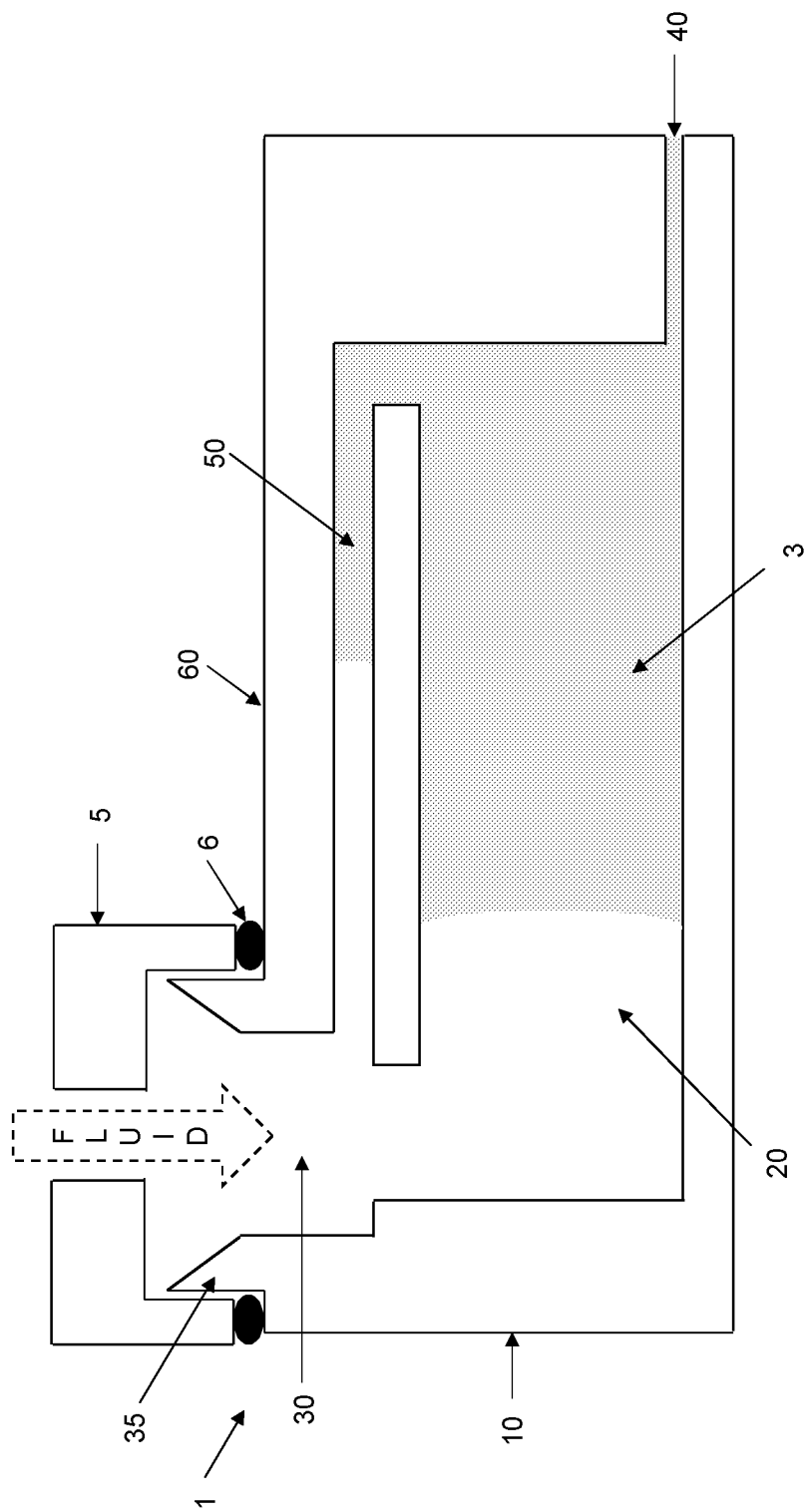
FIG. 15 illustrates the sample loading cartridge according to FIG. 14 during sample ejection.

FIG. 15 illustrates ejection of liquid sample 3 from the sample reservoir 20 of the sample loading cartridge 1 of FIG. 14. In this embodiment, the fluid flow circuitry 5 is preferably arranged around and thereby enclosing the funnel-shaped structure 35 with the seal 6, such as O-ring, circumferentially arranged onto the top part 12 of the cartridge body 10 outside of the funnel-shaped structure 35.

Figure 20:
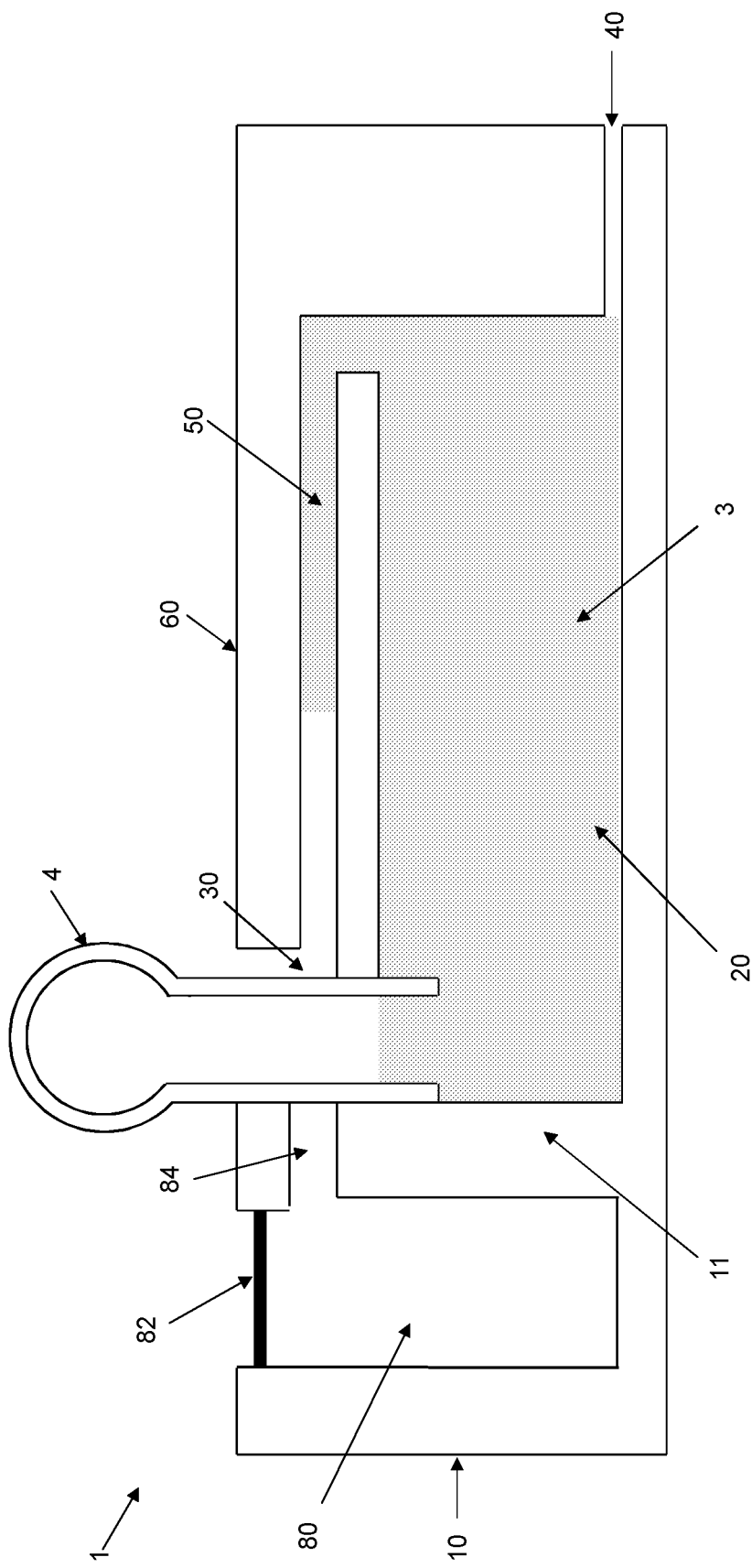
FIG. 20 illustrates a sample loading cartridge according to another embodiment.

FIG. 20 illustrates a further embodiment of the sample loading cartridge 1. This embodiment is designed to prevent or at least minimize contamination between different sample loading cartridges 1 when using a fluid flow circuitry that can be used to eject liquid sample 3 from the different sample loading cartridges 1. The sample loading cartridge comprises an ejection chamber 80 that is in fluid connection with the sample port 30 such as using an ejection channel 84 interconnecting the sample port and the ejection chamber 80. Such an ejection channel 84 is preferably arranged in an upper portion of a wall of the cartridge body 10 separating the ejection chamber 80 from the sample reservoir 20. The ejection channel 84 is in FIG. 20, as an illustrative example, substantially aligned with the feedback channel 20. The embodiments are, however, not limited thereto.

In an embodiment, the ejection chamber 80 is closed or sealed by a septum 82, which closes an opening of the ejection chamber 80 to the outside of the sample loading cartridge 1.

Figure 21:
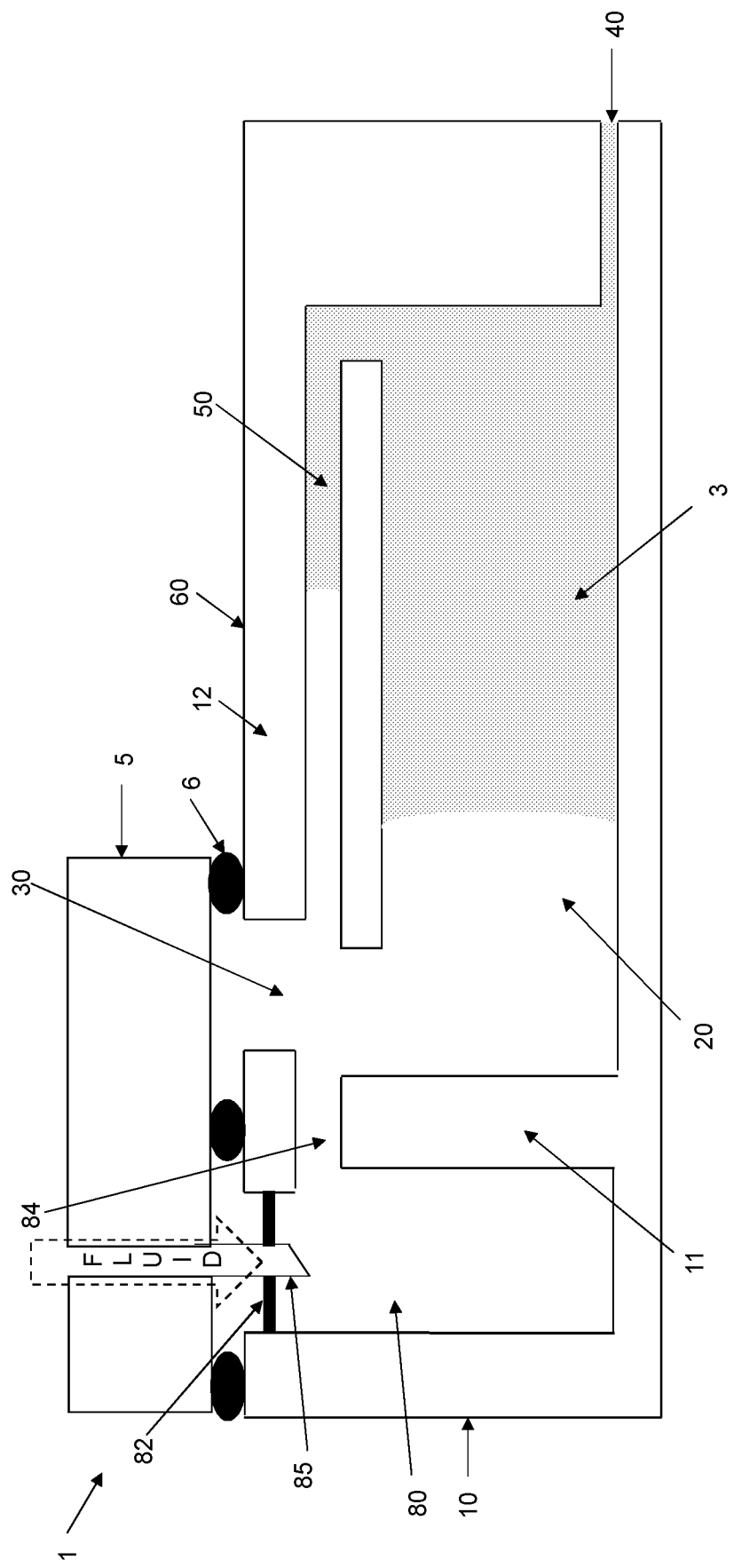
FIG. 21 illustrates the sample loading cartridge according to FIG. 20 during sample ejection.

FIG. 21 illustrates the sample loading cartridge 1 of FIG. 20 during the ejection phase. In this embodiment, the fluid flow circuitry 5 comprises seals 6, such as one or more O-rings, that sealingly contacts and engages with the top part 12 of the cartridge body 10. In more detail, seals 6 are preferably provided to enclose the sample port 30 and the opening of the ejection chamber 80. The fluid flow circuitry 5 preferably comprises a needle 85 or other hollow penetrating structure that is brought into the opening of the ejection chamber 80 and through the septum 82 as shown in FIG. 21. Fluid can then be ejected by the fluid flow circuitry 5 through the needle 82 and into the ejection chamber 80, and further through the ejection channel 82 and into the sample reservoir 20 to thereby eject the liquid sample 3 through the output channel 40.

The fluid flow circuitry 5 is never in contact with the sample reservoir 20 or the liquid sample 3 present therein in this design of the sample loading cartridge 1. In clear contrast, the fluid flow circuitry 5 merely penetrates into the ejection chamber 80 that lacks any liquid sample 3. This means that the risk of cross-contamination when using one and the sample fluid flow circuitry 5 to eject liquid samples 3 contained in sample reservoirs 20 of different sample loading cartridges 1 is minimized or at least significantly reduced as compared to the case when the fluid flow circuitry is designed to eject fluid directly into the sample reservoir 20 through the sample port 30. The embodiment as shown in FIGS. 20 and 21 is therefore preferred in applications where cross-contamination should be minimized.

The embodiments shown in FIGS. 20 and 21 may be combined with any of the embodiments shown in FIGS. 12 to 14.

The sample loading cartridge 1 could be used to load any liquid sample 3. The sample may, for instance, be a biological sample comprising molecules of interest, such as deoxyribonucleic acid (DNA) molecules, ribonucleic acid (RNA) molecules and/or proteins, and/or comprising cells of interest. For instance, the biological sample could be a blood sample, a plasma sample, a urine sample, a saliva sample, a feces sample, a cerebrospinal fluid sample, an amniotic fluid sample, a milk sample, a sputum derived sample or a lymph sample as illustrative, but non-limiting, examples. The liquid sample 3 loaded in the sample loading cartridge 1 could, alternatively, be a liquid sample, such as a buffer sample or an aqueous sample, comprising one or more drugs, test agents or chemicals, such as antibiotics; chemotherapeutic agents; labels, such as chemiluminescent labels, fluorescent labels, radioactive labels and dyes; antibodies; etc.

The sample reservoir 20 of the sample loading cartridge 1 may be empty prior to filling with liquid sample 3. In another embodiment, the sample reservoir 20 could comprise at least one agent prior to filling with liquid sample 3. Such an agent could, for instance, be a lyophilized agent, a dried in agent and/or a pad containing such an agent. Once liquid sample 3 enters the sample reservoir 20 and contacts the at least one agent, the agent(s) will be dissolved in the liquid sample 3 or at least suspended in the liquid sample 3.

As an example, the at least one agent could be a fluorophore or other detectable agent that can be detected in the detection portion 60.

In an embodiment of the sample loading cartridge 1, the detection portion 60 is optional and may therefore be omitted. Such an embodiment, does not allow any detectable feedback to verify that the sample reservoir 20 has been correctly filled with liquid sample 3. However, the embodiment still benefits from an efficient filling of liquid sample 3 due to the presence of the feedback channel 50 having a lower flow resistance as compared to the output channel 40. This means that the feedback channel 50 and its lower flow resistance efficiently prevents or at least significantly reduces the risk of liquid sample 3 entering the output channel 40 during the filling phase.

The sample loading cartridge 1 could be a disposable cartridge 1 intended for one use only. In such a case, once the liquid sample 3 pre-loaded into the sample reservoir 20 has been ejected through the output channel 40, the sample loading cartridge 1 is disposed. Alternatively, the sample loading cartridge 1 could be for multi-use applications, i.e., re-used at least once. Hence, in such a case the sample reservoir 20 of the sample loading cartridge 1 can be subject to multiple cycles of sample loading and sample ejection.

The sample loading cartridge 1 can be manufactured in one piece or as several pieces that are connected together to form the sample loading cartridge 1 using, for example, ultrasonic or laser welding, gluing or other forms of bonding. Illustrative, but non-limiting, examples of materials for the sample loading cartridge 1 and its cartridge body 10 include plastics, such as polyamides (PA), polycarbonate (PC), polyester (PES), polyethylene (PE), high-density polyethylene (HDPE), low-density polyethylene (LDPE), polyethylene terephthalate (PET), polypropylene (PP), polystyrene (PS), polyurethanes (PU), polyvinyl chloride (PVC), polyvinylidene chloride (PVDC), acrylonitrile butadiene styrene (ABS), polyepoxide, polymethyl methacrylate (PMMA), polytetrafluoroethylene (PTFE), phenol formaldehyde (PF), melamine formaldehyde (MF), urea-formaldehyde (UF), polyetheretherketone (PEEK), maleimide/bismaleimide, polyetherimide (PEI), polyimide, plastarch material, polylactic acid (PLA), or a mixture thereof. Also other polymers could be used as material for the sample loading cartridge 1 and its cartridge body 10, such as styrene-ethylene-butylene-styrene (SEBS) polymer and styrene-butadiene-styrene (SBS) polymer. Other materials that can be used for the sample loading cartridge 1 include metal and metal alloys, such as aluminum, copper, titanium, cobalt, nickel, zinc and alloys thereof, steel and other iron alloys, magnesium alloys, CoP alloy, CoC alloy and NAS alloy.

Figure 16:
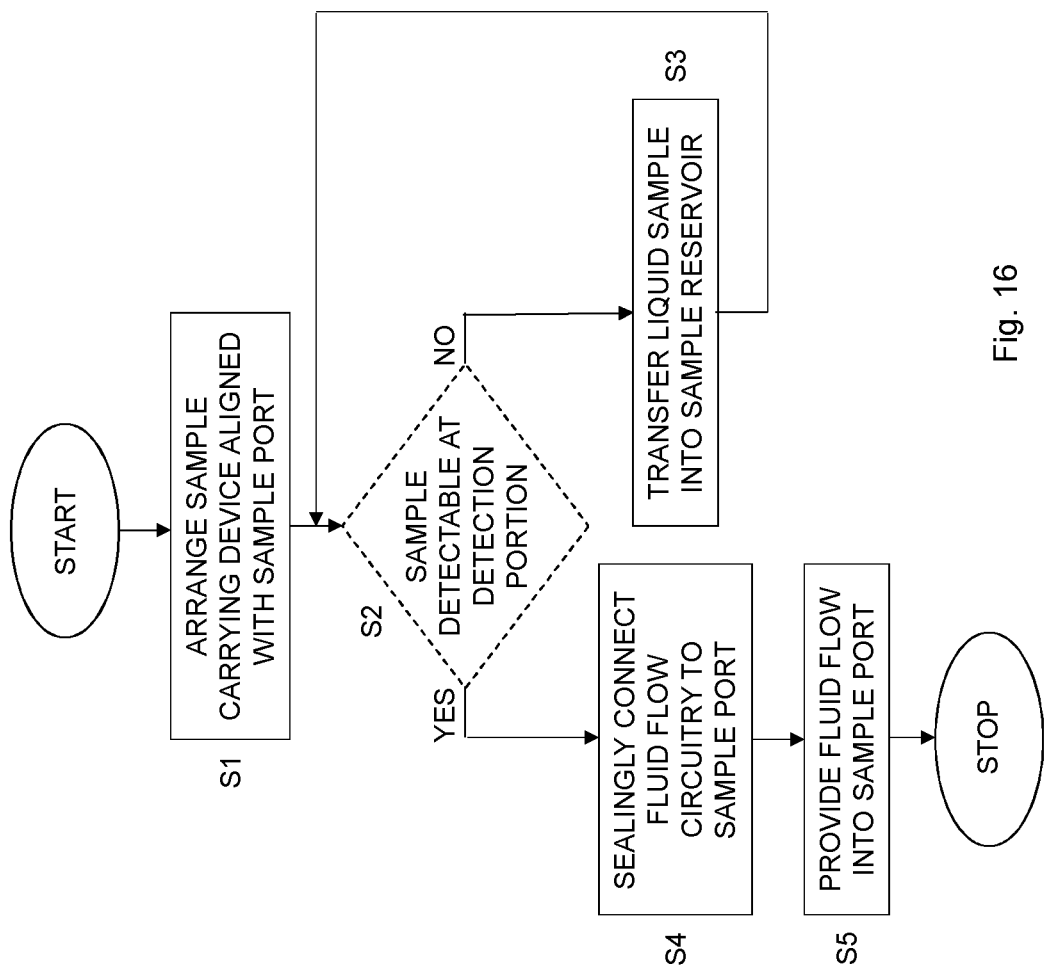
FIG. 16 is a flow chart illustrating a method of loading a sample loading cartridge according to an embodiment.

FIG. 16 is a flow chart illustrating a method of loading a sample loading cartridge 1. The method comprises arranging, in step S1, a sample carrying device 4 aligned with the sample port 30 of a sample loading cartridge 1 according to any of the embodiments. The method also comprises transferring, in step S3, a liquid sample 3 from the sample carrying device 4 into the sample reservoir of the sample loading cartridge 1 through the sample port 30 until liquid sample 3 is detectable in the feedback channel 50 at the detection portion 60 of the cartridge body 10.

In an embodiment, the method also comprises an optional step S2, which comprises monitoring the detection portion 60 of the cartridge body 10 to determine or verify whether there is any liquid sample 3 detectable in the feedback channel 50 at the detection portion 60. This monitoring in step S2 can be performed according to any of the embodiments as disclosed herein, such as visually by a human operator, optically by, for instance, a camera, using electrical measurements or sensor readings. If no liquid sample 3 is detectable in the monitoring of step S2 the method continues to step S3, in which liquid sample 3 is transferred from the sample carrying device 4 into the sample reservoir 20. The loop of steps S2 and S3 is preferably continued until the monitoring in step S2 determines that the liquid sample 3 is detectable in the feedback channel 50 at the detection portion 60 and that the sample reservoir 20 thereby is correctly filled with liquid sample 3. In such a case, the method instead, either directly or at a later point in time, continues to step S4. This step S4 comprises sealingly connecting a fluid flow circuitry 5 to the sample port 30, such as illustrated in FIG. 6, 7, 8 or 15. This embodiment of the method also comprises providing, in step S5, a fluid flow from the fluid flow circuitry 5 into the sample port 30 to eject liquid sample 3 in the sample reservoir 20 out through the output channel 40 of the sample loading cartridge 1. This step S5 may be performed as shown in FIG. 7, 8 or 15.

In an embodiment, step S4 comprises sealingly connecting a fluid flow circuitry 5 comprising a needle 85 to the sample port 30 and the opening of the ejection chamber 80 of the sample loading cartridge 1 as shown in FIG. 21 so that the needle 85 penetrates the septum 82. In this embodiment, step S5 comprises providing S5 a fluid flow from the fluid flow circuitry 5 into the ejection chamber 30 to eject liquid sample 3 in the sample reservoir 20 out through the output channel 40 of the sample loading cartridge 1.

The liquid sample 3 can be ejected from the output channel 40 to any downstream application or appliance, such as a microfluidic device.

Figure 17:
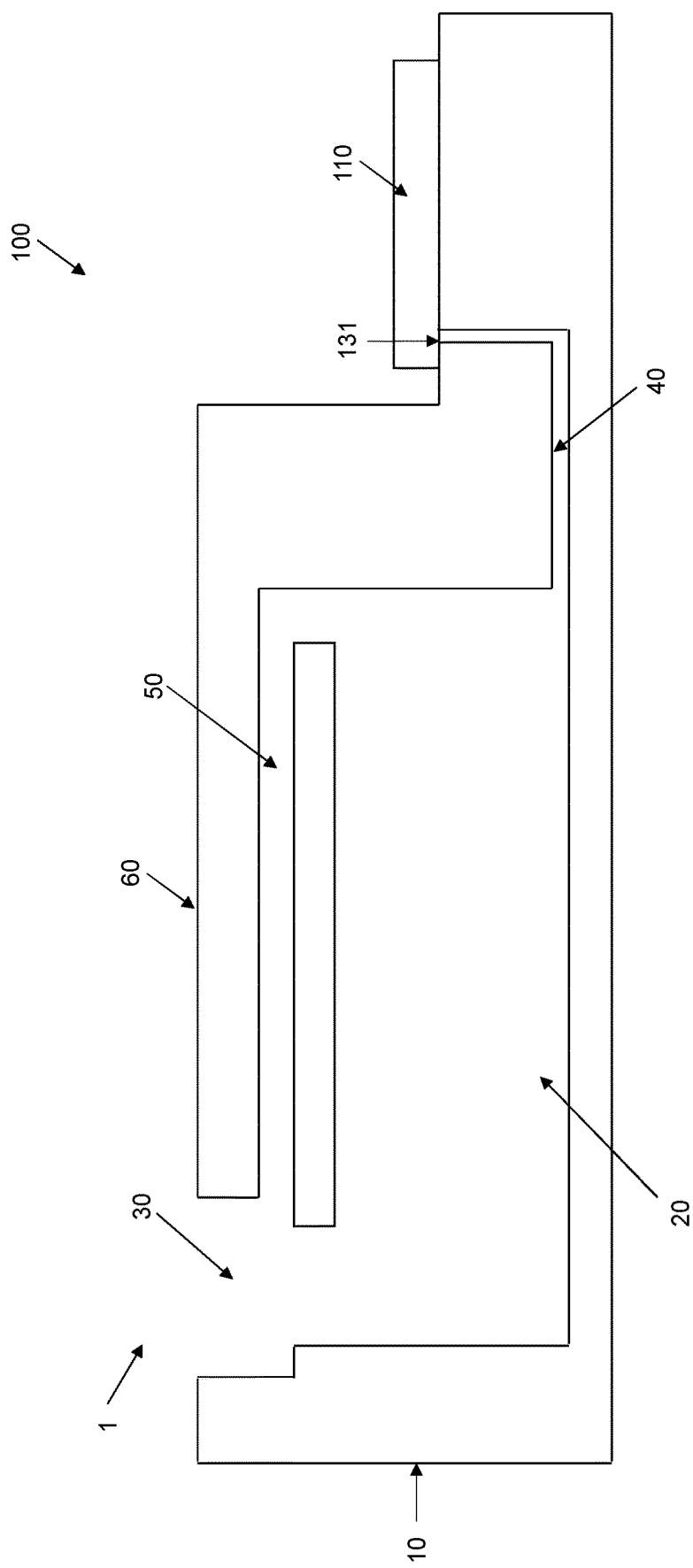
FIG. 17 illustrates a device according to an embodiment.
Figure 18:
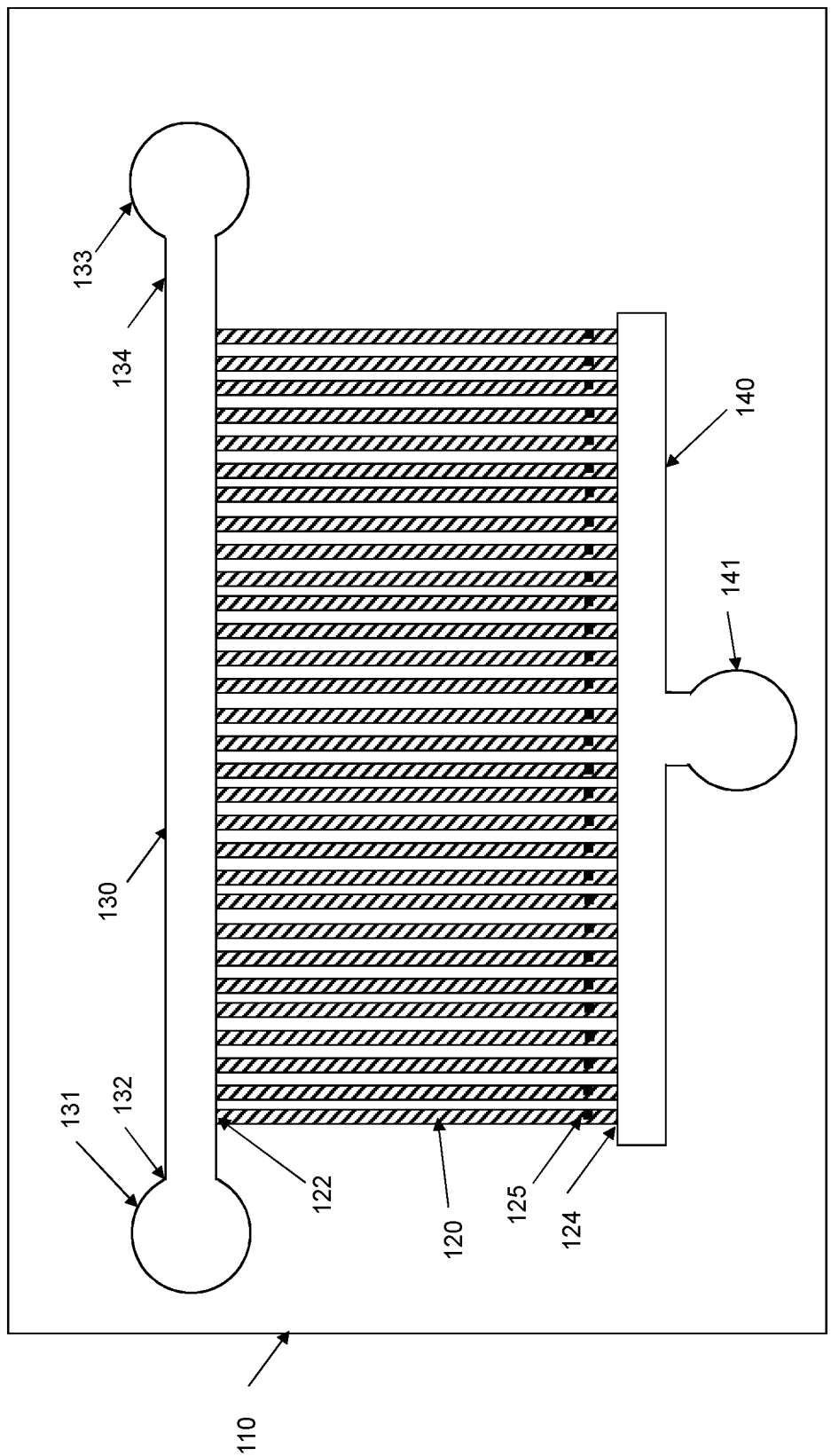
FIG. 18 illustrates a substrate of the device shown in FIGS. 17 and 19.

FIG. 17 illustrates an embodiment of a device 100 comprising a sample loading cartridge 1 according to any of the embodiments. The device 100 also comprises, see FIG. 18, a microfluidic device in the form of a substrate 110 comprising multiple cell channels 120 having a respective first end 122 in fluid connection with a flow input channel 130 and a respective second end 124 in fluid connection with a flow output channel 140. The cell channels 120 comprise a respective channel restriction 125 in connection with the respective second end 124 to prevent target cells entering the cell channels 120 from reaching the flow output channel 140. The output channel 40 of the sample loading cartridge 1 is in fluid connection with the flow input channel 130.

The cell channels 120 in the substrate 110 and preferably also the flow input channel 130 and the flow output channel are preferably microchannels. Hence, the substrate 110 is preferably a microfluidic substrate or device.

The substrate 110 of the device 100 could be designed as disclosed in any of WO 2016/007063, WO 2016/007068 and Baltekin et al., *PNAS* 2017, 114(34): 9170-9175.

In a preferred embodiment, the flow input channel 130 has a first end 132 in fluid connection with a first input port 131, which in turn is in fluid connection with the output channel 40. The flow input channel 130 also has a second end 134, which may optionally be in fluid connection with a second input port 133. The flow output channel 140 in the substrate 110 is in fluid connection with an output port 141.

Figure 19:
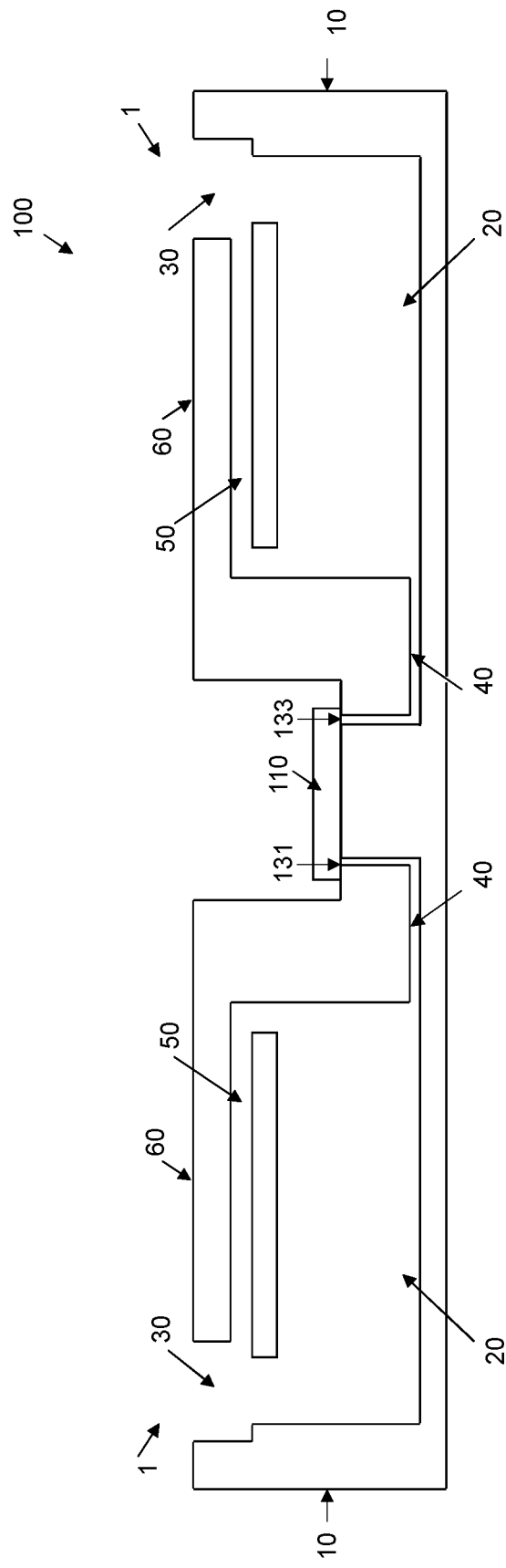
FIG. 19 illustrates a device according to another embodiment.

In another embodiment, see FIG. 19, the first input port 131 of the flow input channel 130 is in fluid connection with the output channel 40 of a first sample loading cartridge 1 comprising a first liquid sample. The second input port 133 of the flow input channel 130 could then be in fluid connection with the output channel 40 of a second sample loading cartridge 1 comprising a second liquid sample. The first and second liquid samples could be a same type of liquid sample or different liquid samples. For instance, the first liquid sample could be a biological sample, such as urine sample, comprising a test agent, such an antibiotic, whereas the second liquid sample is the biological sample lacking the test agent.

In any of these embodiments, the output port 141 could be in fluid connection with the output channel of a third sample loading cartridge 1.

In some embodiments, the substrate 110 may comprise at least two sets of cell channels 120 having a respective flow input channel 130 and a flow output channel 140. In such a case, respective first input ports 131 of the at least flow input channels 130 may be in fluid connection with the output channel 40 of a common sample loading cartridge 1 comprising a first liquid sample. The respective second input ports 133 of the at least two flow input channels 130 are then preferably in fluid connection with the output channel 40 of different sample loading cartridges 1 comprising a second liquid sample, a third liquid sample, and so on. Hence, a common sample loading cartridge 1 is connected to each first input port 131, whereas the respective second input ports 133 are instead in fluid connection with a respective sample loading cartridge 1. The first, second and/or third liquid samples could be a same type of liquid sample or different liquid samples. For instance, the first liquid sample could be a biological sample, such as urine sample containing bacteria, whereas the second liquid sample is a growth media comprising a test agent, such an antibiotic, and the third liquid sample is the growth media lacking the test agent.

In operation, and if the sample reservoir 20 is pre-loaded with a biological sample comprising target cells, the biological sample is ejected from the sample reservoir 20 through the output channel 40 and into the first input port 131 of the flow input channel 130. The biological sample is forced to flow through the cell channels 120 and further into the flow output channel 140 and out through the output port 141. The respective channel restriction 125 in the cell channels 120 will then efficiently prevent or at least restrict or inhibit the target cells present in the biological sample from passing the respective channel restriction 125 and into the flow output channel 140. Hence, target cells present in the biological sample are captured in the cell channels 120.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A sample loading cartridge for a microfluidic device, the sample loading cartridge comprising:
    a cartridge body comprising a sample reservoir configured to house a volume of a liquid sample;
    a sample port in connection with the sample reservoir and configured to receive the liquid sample;
    an output channel connected to and extending from the sample reservoir; and
    a feedback channel connected to the sample reservoir and to the sample port and configured to vent air through the feedback channel as the sample reservoir is filled with liquid sample received from the sample port, wherein
    the cartridge body comprises a detection portion aligned with at least a portion of the feedback channel to enable detection of presence of liquid sample in the feedback channel; and
    a flow resistance of the feedback channel is lower than a flow resistance of the output channel to cause the liquid sample received from the sample port to enter the feedback channel when the sample reservoir is full with liquid sample, with substantially no liquid sample entering the output channel.

2. The sample loading cartridge according to claim 1, wherein the detection portion is a window aligned with the at least a portion of the feedback channel to provide visual access to the feedback channel.

3. The sample loading cartridge according to claim 1, wherein the detection portion comprises at least one electrode arranged to measure an electrical property across the feedback channel.

4. The sample loading cartridge according to claim 1, wherein the detection portion comprises a sensor arranged to detect presence of liquid sample in the feedback channel.

5. The sample loading cartridge according to claim 1, wherein
    the sample port is connected to a ceiling of the sample reservoir; and
    the feedback channel is connected to the ceiling of the sample reservoir and to the sample port.

6. The sample loading cartridge according to claim 5, wherein the output channel is connected to and extends from an end side of the sample reservoir at a position of the end side below the ceiling with regard to an axis extending between a bottom of the sample reservoir and the ceiling.

7. The sample loading cartridge according to claim 1, wherein the flow resistance of the feedback channel is lower than the flow resistance of the output channel to cause liquid sample received in the sample port to enter the feedback channel when the sample reservoir is full of fluid with substantially no liquid sample entering the output channel.

8. The sample loading cartridge according to claim 7, wherein a ratio between the flow resistance of the feedback channel and the flow resistance of the output channel is less than $1/10$.

9. The sample loading cartridge according to claim 8, wherein the ratio between the flow resistance of the feedback channel and the flow resistance of the output channel is less than $1/100$.

10. The sample loading cartridge according to claim 9, wherein the ratio between the flow resistance of the feedback channel and the flow resistance of the output channel is less than $1/1000$.

11. The sample loading cartridge according to claim 1, wherein a cross-sectional area of the feedback channel is larger than a cross-sectional area of the output channel to cause liquid sample received in the sample port to enter the feedback channel with substantially no liquid sample entering the output channel.

12. The sample loading cartridge according to claim 11, wherein a ratio between the cross-sectional area of the output channel and the cross-sectional area of the feedback channel is equal to or smaller than $1/50$.

13. The sample loading cartridge according to claim 12, wherein the ratio between the cross-sectional area of the output channel and the cross-sectional area of the feedback channel is equal to or smaller than $1/75$.

14. The sample loading cartridge according to claim 13, wherein the ratio between the cross-sectional area of the output channel and the cross-sectional area of the feedback channel is equal to or smaller than 1/100.

15. The sample loading cartridge according to claim 1, further comprising an overfill reservoir interposed between the sample port and the sample reservoir, wherein the feedback channel is connected to the sample reservoir and to the overfill reservoir.

16. The sample loading cartridge according to claim 1, wherein the sample port comprises a funnel-shaped structure.

17. The sample loading cartridge according to claim 1, further comprising an ejection chamber in fluid connection with the sample reservoir through an ejection channel, wherein an opening of the ejection chamber is closed by a septum.

18. A device comprising:
a sample loading cartridge according to claim 1; and
a microfluidic device in the form of a substrate comprising multiple cell channels having a respective first end in fluid connection with a flow input channel and a respective second end in fluid connection with a flow output channel, wherein
the cell channels comprise a respective channel restriction in connection with the respective second end to prevent target cells entering the cell channels from reaching the flow output channel; and
the output channel of the sample loading cartridge is in fluid connection with the flow input channel.

19. The device according to claim 18, wherein
the sample loading cartridge is a first sample loading cartridge and the device comprises a second sample loading cartridge comprising:
a cartridge body comprising a sample reservoir configured to house a volume of a liquid sample;
a sample port in connection with the sample reservoir and configured to receive the liquid sample;
an output channel connected to and extending from the sample reservoir; and
a feedback channel connected to the sample reservoir and to the sample port and configured to vent air through the feedback channel as the sample reservoir is filled with liquid sample received from the sample port, wherein
the cartridge body comprises a detection portion aligned with at least a portion of the feedback channel to enable detection of presence of liquid sample in the feedback channel; and a flow resistance of the feedback channel is lower than a flow resistance of the output channel to cause the liquid sample received from the sample port to enter the feedback channel when the sample reservoir is full with liquid sample, with substantially no liquid sample entering the output channel;
the output channel of the first sample loading cartridge is in fluid connection with a first input port of the flow input channel; and
the output channel of the second sample loading cartridge is in fluid connection with a second input port of the flow input channel.

20. A method of loading a sample loading cartridge, the method comprising:
arranging a sample carrying device aligned with the sample port of a sample loading cartridge according to claim 1; and
transferring a liquid sample from the sample carrying device into the sample reservoir of the sample loading cartridge through the sample port until liquid sample is detectable in the feedback channel at the detection portion of the cartridge body.

21. The method according to claim 20, further comprising:
sealingly connecting a fluid flow circuitry to the sample port; and
providing a fluid flow from the fluid flow circuitry into the sample port to eject liquid sample in the sample reservoir out through the output channel of the sample loading cartridge.

22. The method according to claim 20, wherein the sample loading cartridge further comprises an ejection chamber in fluid connection with the sample reservoir through an ejection channel, and wherein an opening of the ejection chamber is closed by a septum, the method further comprising:
sealingly connecting a fluid flow circuitry comprising a needle to the sample port and the opening of the ejection chamber of the sample loading cartridge so that the needle penetrates the septum; and
providing a fluid flow from the fluid flow circuitry into the ejection chamber to eject liquid sample in the sample reservoir out through the output channel of the sample loading cartridge.

* * * * *